(12) United States Patent
Abbott et al.

(10) Patent No.: US 11,712,423 B2
(45) Date of Patent: Aug. 1, 2023

(54) METHODS AND COMPOSITIONS FOR MODIFYING MUCOUS MEMBRANES

(71) Applicants: Nicholas L. Abbott, Madison, WI (US); Christopher J. Murphy, Madison, WI (US)

(72) Inventors: Nicholas L. Abbott, Madison, WI (US); Christopher J. Murphy, Madison, WI (US)

( * ) Notice: Subject to any disclaimer, the term of this patent is extended or adjusted under 35 U.S.C. 154(b) by 59 days.

(21) Appl. No.: 17/222,089

(22) Filed: Apr. 5, 2021

(65) Prior Publication Data

US 2021/0244676 A1    Aug. 12, 2021

Related U.S. Application Data

(63) Continuation of application No. 16/000,147, filed on Jun. 5, 2018, now Pat. No. 10,966,935, which is a continuation of application No. 14/908,927, filed as application No. PCT/US2014/048391 on Jul. 28, 2014, now Pat. No. 9,987,235.

(60) Provisional application No. 61/861,247, filed on Aug. 1, 2013.

(51) Int. Cl.

| | |
|---|---|
| *A61K 38/17* | (2006.01) |
| *A61K 47/42* | (2017.01) |
| *A61K 9/70* | (2006.01) |
| *A61K 48/00* | (2006.01) |
| *A61K 9/00* | (2006.01) |
| *A61K 45/06* | (2006.01) |
| *A61K 31/00* | (2006.01) |
| *A61K 31/095* | (2006.01) |
| *A61K 31/375* | (2006.01) |
| *A61K 31/66* | (2006.01) |
| *A61K 31/70* | (2006.01) |
| *A61K 31/7088* | (2006.01) |
| *A61K 31/726* | (2006.01) |
| *A61K 38/02* | (2006.01) |
| *A61K 38/05* | (2006.01) |

(52) U.S. Cl.
CPC ............. *A61K 9/70* (2013.01); *A61K 9/006* (2013.01); *A61K 9/0014* (2013.01); *A61K 9/0034* (2013.01); *A61K 9/0043* (2013.01); *A61K 9/0048* (2013.01); *A61K 31/00* (2013.01); *A61K 31/095* (2013.01); *A61K 31/375* (2013.01); *A61K 31/66* (2013.01); *A61K 31/70* (2013.01); *A61K 31/7088* (2013.01); *A61K 31/726* (2013.01); *A61K 38/02* (2013.01); *A61K 38/05* (2013.01); *A61K 38/1735* (2013.01); *A61K 45/06* (2013.01); *A61K 47/42* (2013.01); *A61K 48/0075* (2013.01)

(58) Field of Classification Search
CPC .... A61K 9/0048; A61K 9/006; A61K 9/0034; A61K 38/1735; A61K 47/42; A61K 48/0075; C07K 1/1072; C07K 14/4727
See application file for complete search history.

(56) References Cited

U.S. PATENT DOCUMENTS

| | | | |
|---|---|---|---|
| 4,615,697 A | 10/1986 | Robinson | |
| 5,552,452 A | 9/1996 | Khadem | |
| 9,987,235 B2 | 6/2018 | Abbott | |
| 10,966,935 B2 * | 4/2021 | Abbott | ................ A61K 31/726 |
| 2003/0087960 A1 * | 5/2003 | Burstein | ................ A61K 31/19 |
| | | | 424/666 |
| 2004/0043432 A1 | 3/2004 | Rowling et al. | |
| 2004/0151774 A1 | 8/2004 | Pauletti | |
| 2004/0266684 A1 | 12/2004 | Smith et al. | |
| 2007/0053844 A1 | 3/2007 | Watanabe | |
| 2008/0317765 A1 | 12/2008 | Izraeli et al. | |
| 2009/0010914 A1 | 1/2009 | Taylor et al. | |
| 2011/0130783 A1 | 6/2011 | Levy | |
| 2012/0141410 A1 | 6/2012 | Torfi | |
| 2012/0165272 A1 * | 6/2012 | Holgersson | ............. A61P 27/02 |
| | | | 530/391.7 |

FOREIGN PATENT DOCUMENTS

WO     2008/067403     6/2008

OTHER PUBLICATIONS

International Search Report & Written Opinion, International Patent Application No. PCT/US2014/048391, dated Jan. 14, 2015.
Davidovich-Pinhas et al. Novel mucoadhesive system based on sulfhydryl-acrylate interactions. Journal of Materials Sciences: Materials in Medicine. 2010, vol. 21, pp. 2027-2034.

* cited by examiner

*Primary Examiner* — Jeffrey E. Russel
(74) *Attorney, Agent, or Firm* — Casimir Jones SC; J. Mitchell Jones

(57) ABSTRACT

The present invention relates to methods and compositions for modifying mucous membranes. In particular, the present invention relates to treating diseases associated with mucous membranes by changing the intrinsic chemical composition and/or physical features of a target mucous membrane.

5 Claims, 1 Drawing Sheet
Specification includes a Sequence Listing.

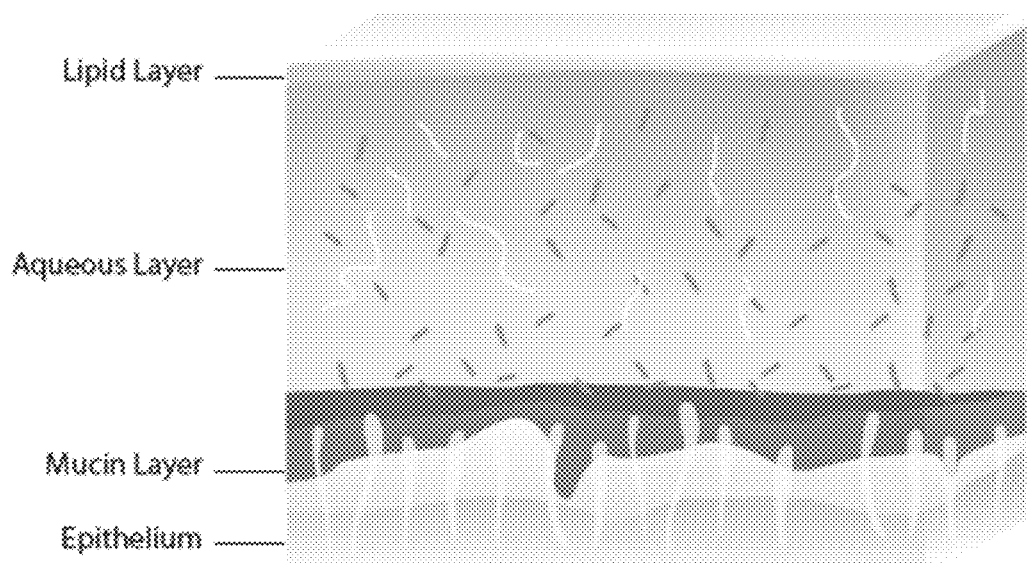

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial sequence
<220> FEATURE:
<223> OTHER INFORMATION: Synthetic

<400> SEQUENCE: 1

Glu Glu Glu Asp
1

<210> SEQ ID NO 2
<211> LENGTH: 21
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (8)..(21)
<223> OTHER INFORMATION: amino acids 8-14 and 15-21 can either be
      present or absent.

<400> SEQUENCE: 2

Lys Leu Ala Lys Lys Leu Ala Lys Leu Ala Lys Lys Leu Ala Lys Leu
1               5                   10                  15

Ala Lys Lys Leu Ala
            20

<210> SEQ ID NO 3
<211> LENGTH: 21
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (8)..(21)
<223> OTHER INFORMATION: amino acids 8-14 and 15-21 can either be
      present or absent.

<400> SEQUENCE: 3

Lys Leu Ala Lys Leu Ala Lys Lys Leu Ala Lys Leu Ala Lys Lys Leu
1               5                   10                  15

Ala Lys Leu Ala Lys
            20

<210> SEQ ID NO 4
<211> LENGTH: 21
<212> TYPE: PRT
<213> ORGANISM: Artificial sequence
<220> FEATURE:
<223> OTHER INFORMATION: Synthetic

<400> SEQUENCE: 4

Lys Ala Leu Lys Ala Leu Lys Lys Ala Leu Lys Ala Leu Lys Lys Ala
1               5                   10                  15

Leu Lys Ala Leu Lys
            20

<210> SEQ ID NO 5
<211> LENGTH: 21
<212> TYPE: PRT
<213> ORGANISM: Artificial sequence
<220> FEATURE:
```

```
<223> OTHER INFORMATION: Synthetic
<220> FEATURE:
<221> NAME/KEY: Xaa
<222> LOCATION: (8)..(21)
<223> OTHER INFORMATION: amino acids 8-14 and 15-21 can either be
      present or absent.

<400> SEQUENCE: 5

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 6
<211> LENGTH: 21
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (8)..(21)
<223> OTHER INFORMATION: amino acids 8-14 and 15-21 can either be
      present or absent.

<400> SEQUENCE: 6

Lys Ala Ala Lys Lys Ala Ala Lys Ala Ala Lys Lys Ala Ala Lys Ala
1               5                   10                  15

Ala Lys Lys Ala Ala
            20
```

METHODS AND COMPOSITIONS FOR MODIFYING MUCOUS MEMBRANES

CROSS-REFERENCE TO RELATED APPLICATIONS

This application is a continuation of U.S. patent application Ser. No. 16/000,147, filed Jun. 5, 2018, now U.S. Pat. No. 10,966,935, which is a continuation of U.S. patent application Ser. No. 14/908,927, filed Jan. 29, 2016, now U.S. Pat. No. 9,987,235, which is a 371 U.S. National Phase Entry of International Patent Application No. PCT/US2014/048391, International Filing Date Jul. 28, 2014, which claims priority to U.S. Provisional Patent Application No. 61/861,247, filed Aug. 1, 2013.

REFERENCE TO A SEQUENCE LISTING

Filed herewith and expressly incorporated herein by reference is a Sequence Listing submitted electronically as an ASCII text file via EFS-Web.
File Name: Size: Created:
33466-US-4-CON_ST25.txt 3,000 bytes Apr. 5, 2021

FIELD OF THE INVENTION

The present invention relates to methods and compositions for modifying mucous membranes and creating new mucous membranes and mimics of mucous membranes. In this application, we define the mucous membrane as the cellular covering exposed to the environment that lines the ocular, gastrointestinal, respiratory and urogenital systems. When using the term mucous membrane, we intentionally include the thin fluid films that are intimately associated with the cellular components and are responsible for wetting of the mucous membrane surface. Additionally, though not always used in this fashion, we include the cornea (that under normal conditions lacks mucous secreting cells) as a component of the mucous membrane of the ocular surface. In particular, the present invention relates to treating diseases associated with mucous membranes and, more broadly, improving and modifying the performance of mucous membranes of vertebrates, by changing the intrinsic chemical composition and/or physical features of target mucous membranes. Methods are described also for identification of agents that interact with said altered mucous membrane or said unaltered mucous membrane for improving the formation and stability of thin films associated with said mucous membrane.

The present invention also includes employment of solutions, emulsions, ointments and transferable thin films (exemplified by but not limited to polyelectrolyte multilayers) that are specifically designed to interact with the said modified mucous membrane to have a therapeutic effect.

BACKGROUND OF THE INVENTION

Mucous membranes have epithelial constituents that possess an intrinsic surface chemistry and the most superficial layer of cells have nano through micron scale topographic features in the form of microvilli and microplicae. The topographic features interact with the thin fluid films in intimate association with the cellular constituents and likely contribute to the relative stability of the thin films. It is known that these surface topographic features can be altered in disease states of the ocular surface and such alterations may contribute to thin film instability. Thin films of fluids, including but not limited to tears, saliva, gastrointestinal coatings, thin films associated with the respiratory tract (nasal passages, trachea, bronchi, bronchioles and alveoli) and cervico-vaginal secretions and thin films associated with the rest of the female reproductive tract, cover the cellular elements of mucous membranes in all vertebrate species. Tatematsu et al., Bone Marrow Transplant. 2012 March; 47(3):416-25. doi: 10.1038/bmt.2011.89. Epub 2011 May 16. The secretions covering mucous membranes come from a variety of sources, and have three broad classes of constituents. The glycosaminoglycan (or mucous) layer; aqueous components containing soluble species such as proteins, sugars, salts and osmolytes; and in the case of tears and to a degree other mucous membranes, a lipid-containing component. The mucous membrane thin films come from cells embedded in the mucous membranes (or proximal to the mucous membranes) or from glandular structures. Water forms the basis of lubrication in the human body, but is unable to provide sufficient lubrication without additives. The importance of biolubrication becomes evident upon aging and disease, particularly under conditions that affect secretion or composition of body fluids. Insufficient biolubrication, may impede proper speech, mastication and swallowing, underlie excessive friction and wear of articulating cartilage surfaces in hips and knees, cause vaginal dryness, and result in dry, irritated eyes. Biolubrication is due to a combination of structure and glycosylation of adsorbed protein films, providing an important clue to design effective therapeutics to restore biolubrication in patients with insufficient biolubrication. Veeregowda et al., PLoS One. 2012; 7(8):e42600. doi: 10.1371/journal.pone.0042600. Epub 2012 Aug. 15.

As a non-limiting example, a widely accepted model of the tear film that coats the ocular surface is one that is comprised of three major constituents; an oily layer derived from glands that line the lid margin (Meibomian or tarsal glands); an aqueous layer derived from lacrimal and accessory lacrimal glands (with admixed soluble proteins as well as admixed lipids and mucins); and a mucin layer derived from goblet cells associated with the conjunctiva as well as mucins that originate from the epithelial cells themselves. See FIG. 1. The mucin constituents form a layer immediately adjacent to the cellular elements of the ocular surface and are thought to associate to a degree with the glycocalyx of the most superficial epithelial cells, as well as being admixed in the thicker aqueous component. The mucin elements are thought to be important for maintaining the stability of the tear film by affecting the surface tension of the cellular interface. The aqueous layer is the thickest component of the tear film and contains a variety of solutes for maintaining ocular health. Immunoglobulins, lysozyme, transferrin, antimicrobial peptides and other constituents assist in controlling bioburden and decreasing the risk of infection. Mucins can also be admixed within this layer. Additionally, growth factors, cytokines and other cytoactive factors are found within the aqueous layer. The oily layer is the outermost layer and provides lubrication as well as decreasing rates of evaporation of the aqueous component of the tear film.

A number of diseases and conditions are associated with dry or dysfunctional mucous membranes. These are exemplified by, but not limited to, dry eye, dry mouth, vaginal drying and diseases involving deficiencies/dysregulation in respiratory thin film coatings. What is needed are safe, effective, and flexible means for treating dry or dysfunctional mucous membrane diseases as well as therapies aimed at improving the performance of non-diseased mucous membranes, that are mediated through alteration of the chemical and or biophysical attributes (including attributes associated with equilibrium and dynamic events in mucous membrane systems) of mucous membranes and/or employment of topical agents that are specifically designed for augmenting thin film (e.g., tear film and thin film coatings of the oral, alimentary, female reproductive and respiratory tracts) performance and its interaction with the cellular constituents of the mucous membrane (such as the ocular surface). In some embodiments, this novel therapeutic platform will employ topical agents specifically chosen to improve surface film performance through interactions with a cellular surface or mucous membrane system surface whose surface chemistry and or biophysical attributes have been altered. In other cases, the topical agents will facilitate the beneficial interaction of existing components of the thin fluid films intimately associated with the cellular constituents of mucous membranes to provide beneficial effect (including to facilitate transport of the existing component to a new location in the mucous membrane system). Broad characteristics indicative of improving the health of the mucous membrane would be an increase in thin fluid film stability (e.g. in the case of the ocular surface an expanded tear break up time), decrease in cellular damage, increased comfort or satisfaction with performance of mucous membrane on the part of the patient, a decrease in the number of application of other palliative coatings and or surface active agents and a decrease in clinical symptoms. In the case of the use of surfactants with RDS in infants, an improved therapeutic effect of administered surfactants as determined by a variety of patient outcomes including but not limited to an increased therapeutic benefit, decrease in the number of re-treatments needed and a decrease in the time required for mechanical ventilatory assistance. The methods should be adaptable without regard to the type of the mucous membrane, or the nature of the patient population, to which the subject belongs.

SUMMARY OF THE INVENTION

The present invention relates to methods and compositions for modifying mucous membranes. In particular, the present invention relates to treating diseases associated with mucous membranes and improving the performance of non-diseased mucous membranes, by changing the intrinsic chemical composition, viscoelastic properties, rheological properties, and/or other biophysical attributes of a target mucous membrane such as charge, surface energy, topography, hydrophilicity, and hydrophobicity.

In some embodiments, the present invention provides a composition for modifying a mucous membrane comprising a first agent that physically interacts or reacts with one or more components of said mucous membrane and/or it's intimately associated adherent thin fluid film and a physiologically acceptable carrier. In some embodiments, the physiologically acceptable carrier is compatible with a mucous membrane. In some embodiments, the first agent physically interacts or reacts with the cellular surface constituents of the mucous membrane including but not limited to mucins associated with cellular constituents, soluble mucins in the thin fluid film associated with the cellular elements, other membrane associated proteins, lipids, constituents of the glycocalyx and associated constituents, and carbohydrates. In some embodiments this will be the glycosaminoglycans of the mucous membrane. In some embodiments, the intimately adherent thin film is selected from the group consisting of a tear film, cervico-vaginal or other component of the female reproductive tract fluid, respiratory thin film coating or thin films associated with the gastrointestinal tract including the oral cavity and thin films associated with the respiratory tract including the nasal cavity, oropharynx, trachea, bronchi, bronchioles and alveoli of the lung. In some embodiments, the component is an aqueous component. In some embodiments, the component is a lipid component. In some embodiments, the components of the mucous membrane are selected from the group consisting of lipids, proteins, glycoaminoglycans (typified by but not limited to the wide variety of mucins associated with mucous membranes), nucleic acids and carbohydrates or groups physically or chemically associated with either of these components. In some embodiments, the first agent is selected from the group consisting of reducing agents, homobifunctional linkers, heterobifunctional linkers, organic molecules comprising a reactive group, organic molecules comprising a click chemistry functionality, organic molecules comprising a photoactivatable group, agents that bind to one or more of lipids, carbohydrates, glycoaminoglycans, nucleic acids and proteins, sensitizing agents, polymers, oligomers, multimers, dendrimers, surfactants, colloidal species, beads, nanoparticles and microparticles (including micro and nanoparticles with shapes tailored to be non-spherical). In some embodiments, the reducing agents are selected from the group consisting of TCEP, ascorbic acid, dithiothreitol and glutathione. In some embodiments, the homobifunctional linkers are selected from the group consisting of N-hydroxysuccinimidyl ester (e.g., including, but not limited to, disuccinimidyl ester, dithiobis(succinimidylpropionate), 3,3'-dithiobis(sulfosuccinimidylpropionate), disuccinimidyl suberate, bis(sulfosuccinimidyl)suberate, disuccinimidyl tartarate, disulfosuccinimidyl tartarate, bis[2-(succinimidyloxycarbonyloxy) ethyllsulfone, bis[2-(sulfosuccinimidooxycarbonyloxy) ethyllsulfone, ethylene glycolbis(succinimidylsuccinate), ethylene glycolbis(sulfosuccinimidylsuccinate), disuccinimidyl glutarate, and N,N'-disuccinimidylcarbonate). In some embodiments, the heterobifunctional linkers are selected from the group consisting of N-succinimidyl 3-(2-pyridyldithio)propionate, succinimidyl 6-(3-[2-pyridyldithiol-propionamido)hexanoate, sulfosuccinimidyl 6-(3'-[2-pyridyldithiol-propionamido)hexanoate, succinimidyloxycarbonyl-α-methyl-α-(2-pyridyldithio)toluene, sulfosuccinimidyl-6-[α-methyl-α-(2-pyridyldithio)toluamidolhexanoate, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl) aminobenzoate, sulfo-succinimidyl(4-iodoacetyl) aminobenzoate, succinimidyl (p-maleimidophenyl)butyrate, sulfosuccinimidyl-4-(p-maleimidophenyl)butyrate, N-(γ-maleimidobutyryloxy)succinimide ester, N-(γ-maleimidobutyryloxy)sulfosuccinimide ester, succinimidyl 6-((iodoacetyl)amino)hexanoate, succinimidyl 6-(6-(((4-iodoacetyl)amino)hexanoyl)amino)hexanoate, succinimidyl 4-(((iodoacetyl)amino)methyl)cyclohexane-1-carboxylate, succinimidyl iodoacetyl)amino)methyl)cyclohexane-1-carbonyl)amino)-hexanoate, and p-nitrophenyl iodoacetate.

In some embodiments, the organic molecules comprising a reactive group are selected from the group consisting of amino acids, peptides, polypeptides, proteins, lipids, carbohydrates, glycoaminoglycans, nucleic acids and combinations thereof, wherein said organic molecules either naturally comprise or a modified to comprise a reactive group. In some embodiments, the organic molecules comprising a reactive group are selected from non-natural organic molecules, including, molecules containing esters, amides, ethers, imides, nitrile, carboxylic acids, hydroxyl, methyl, methylene, alkene and alkyne groups. In some embodiments, the organic molecules comprising a click chemistry functionality are selected from the group consisting of amino acids, peptides, polypeptides, proteins, lipids, carbohydrates, glycoaminoglycans, nucleic acids and combinations thereof, wherein said organic molecules either naturally comprise or a modified to comprise a click chemistry functionality. In some embodiments, the organic molecules comprising a photoactivatable group are selected from the group consisting of amino acids, peptides, polypeptides, proteins, lipids, carbohydrates, glycoaminoglycans, nucleic acids and combinations thereof, wherein said organic molecules either naturally comprise or a modified to comprise a reactive group.

In some embodiments, the agents that bind to one or more of lipids, carbohydrates, glycoaminoglycans and proteins is selected from the group consisting of an antigen binding protein, a lectin, a dendrimer, an aptamer, and a nucleic acid.

In some embodiments, the first agent further comprises a first binding partner moiety that is capable of interaction with a second binding partner moiety. In some embodiments, the first binding partner moiety is selected from the group consisting of a small organic molecule, biotin, a polymer, an oligomer, a hapten, nucleic acid, an oligopeptide, a polypeptide and carbohydrate. In some embodiments, the first binding partner reacts with the second binding partner to form a covalent or non-covalent bond. In some embodiments, the sensitizing agent is selected from the group consisting of redox-sensitizers, photosensitizers, radiation sensitizers and chemical and physical sensitizers.

In some embodiments, the compositions further comprise a second agent that promotes holding an aqueous component of said mucous membrane in place. In some embodiments, the mucous membrane component is a tear film and said agent promotes holding an aqueous or lipid component of said tear film in place to increase tear break-up time. In some embodiments, the second agent is selected from the group consisting of mucins, synthetic mucins, mucin analogs, dendrimers, nano- and microscale particles and their assemblies, particles with chemical patches, and aspherical particles, hydrogels, polyelectrolytes, polyelectrolyte multilayers, polymers, amphiphiles, polymeric amphiphiles, surfactants, hydrophilic polymers, cross-linked hydrophilic polymers, deliquescent molecules, nanoporous substances, nanostructured hydrogels, polymeric scaffolds, hyaluronic acid, polymeric brushes, cross-linked collagen, photoactivatable crosslinkers, riboflavin cross-linkers, modified celluloses, hydroxypropylcellulose, hydroxymethylcellulose, dextrans, glycerin, metal salts, polyethyleneglycol, liquid crystals, rheological modifiers, modifiers of disjoining pressures, charged agents and non-charged agents, agents that modify the topography of mucous membrane systems, agents the lead to chemical and physical heterogeneity in mucous membrane systems, and combinations thereof.

In some embodiments, the composition further comprises a drug agent. In some embodiments, the drug agent is select from the group consisting of anti-inflammatory drugs, antimicrobial drugs (including but not limited to anti-viral, antibacterial, antifungal, antiparasitic), immune modulating drugs, vitamins, topically acting anesthetics and analgesics.

In some embodiments, the present invention provides a topical formulation comprising a composition as described above. In some embodiments, the first agent interacts or reacts with the native surface chemistry of said mucous membrane.

In some embodiments, the present invention provides a system comprising a composition as described above and at least one additional topical agent that interacts or reacts with said first agent to improve performance parameters and/or stability. In some embodiments, the at least one additional topical agent is selected from the group consisting of mucins, synthetic mucins, mucin analogs, dendrimers, nano- and microscale particles, hydrogels, polyelectrolytes, polyelectrolyte multilayers, hydrophilic polymers, cross-linked hydrophilic polymers, deliquescent molecules, nanoporous substances, nanostructured hydrogels, polymeric scaffolds, hyaluronic acid, polymeric brushes, cross-linked collagen, photoactivatable crosslinkers, riboflavin cross-linkers, modified celluloses, hydroxypropylcellulose, hydroxymethylcellulose, dextrans, glycerin, metal salts, polyethyleneglycol, liquid crystals, and combinations thereof. In some embodiments, the at least one additional topical agent is different from said first agent. In some embodiments, the at least on additional topical agent comprises a second binding partner moiety that interacts with said first binding partner moiety.

In some embodiments, the present invention provides methods of treating a mucous membrane in a subject comprising applying a composition system or formulation as described above. In some embodiments, the mucous membrane is selected from ocular, vaginal, oral, nasal, respiratory and alimentary mucous membranes. In some embodiments, the mucous membrane is an ocular mucous membrane and said treating increasing tear break-up time. In some embodiments, the subject is suffering from a disease of the ocular mucous membrane. In some embodiments, the disease is dry eye. In some embodiments, the subject is suffering from dry mouth. In some embodiments the subject is suffering from a dry nose. In some embodiments the subject is suffering from cystic fibrosis. In some embodiments the subject is a premature infant and is suffering from respiratory distress syndrome. In some embodiments, the subject is a human subject. In some embodiments, the subject is a selected from the group consisting of a stock animals and a companion animals. In some embodiments the subject is a non-traditional pet exotic animal (fish, avian, reptile, amphibian, bird, exotic mammal). In some embodiments, the composition is applied via a contact lens. In some embodiments, the subject is not diseased and the composition improves the performance of the subject's mucous membrane system. In some embodiments, application of said composition improves the experience of wearing said contact lens. In some embodiments, the composition is applied as a formulation selected from the group consisting of a dissolvable plug or sheet, drop, a spray, a solution, a suspension, a cream, an emulsion, a particulate, a lipid assembly such as a liposome or vesicle, a lotion and an ointment. In some embodiments, a hyperosmotic solution is applied to the mucous membrane before or after treatment with said composition.

In some embodiments, the present invention provides method of treating a mucous membrane in a subject comprising applying a composition, system or formulation as described above to a mucous membrane followed by the addition of said at least one topical agent. In some embodiments, the mucous membrane is selected from ocular, vaginal, oral, nasal and intestinal mucous membranes. In some embodiments, the mucous membrane is an ocular mucous membrane and said treating increasing tear break-up time. In some embodiments, the subject is suffering from a disease of the ocular mucous membrane. In some embodiments, the disease is dry eye. In some embodiments, the subject is suffering from dry mouth. In some embodiments, the subject is a human subject. In some embodiments, the subject is a selected from the group consisting of stock animals and a companion animals. In some embodiments the subject is a non-traditional pet exotic animal (e.g., fish, avian, reptile, amphibian, bird, exotic mammals). In some embodiments, the composition is applied via a contact lens. In some embodiments, application of said composition improves the experience of wearing said contact lens. In some embodiments, the composition is applied as a formulation selected from the group consisting of a dissolvable plug or sheet, drop, a spray, a solution, a suspension, a cream, a lotion and an ointment. In some embodiments, a hyperosmotic solution is applied to the mucous membrane before or after treatment with said composition.

In some embodiments, the present invention provides a dissolvable plug comprising a composition as described above. In some embodiments, the present invention provides a system comprising a first dissolvable plug comprising a composition as described above and at least a second dissolvable plug comprising at least one topical agent as described above.

In some embodiments, the present invention provides a composition as described above and an applicator for applying said composition to a mucous membrane. In some embodiments, the kits further comprise a topical agent administration to said mucous membrane after application of said composition. In some embodiments, the composition is provided as a formulation selected from the group consisting of a dissolvable plug, drop, a spray, a solution, a suspension, a cream, a lotion and an ointment. In some embodiments, the topical agent is provided as a formulation selected from the group consisting of a dissolvable plug, drop, a spray, a solution, a suspension, a cream, a lotion and an ointment.

In some embodiments, the present invention provides a topical administration formulation comprising the composition as described above, wherein said composition is provided as a formulation selected from the group consisting of a dissolvable plug, drop, a spray, a solution, a suspension, a cream, a lotion and an ointment.

In some embodiments, the present invention provides methods comprising applying a sensitizing agent to a mucous membrane and then irradiating said mucous membrane to activate said sensitizing agent. In some embodiments, the irradiating occurs in the presence of a second agent. In some embodiments, the second agent is applied after said irradiating. In some embodiments, the second agent is selected from the group consisting of reducing agents, homobifunctional linkers, heterobifunctional linkers, organic molecules comprising a reactive group, organic molecules comprising a click chemistry functionality, organic molecules comprising a photoactivatable group, agents that bind to one or more of lipids, carbohydrates, glycoaminoglycans, nucleic acids and proteins, polymers, oligomers, multimers, dendrimers, surfactants, colloidal species, beads, nanoparticles and microparticles, mucins, synthetic mucins, mucin analogs, dendrimers, nano- and microscale particles, hydrogels, polyelectrolytes, polyelectrolyte multilayers, polymers, amphiphiles, surfactants, hydrophilic polymers, cross-linked hydrophilic polymers, deliquescent molecules, nanoporous substances, nanostructured hydrogels, polymeric scaffolds, hyaluronic acid, polymeric brushes, cross-linked collagen, photoactivatable crosslinkers, riboflavin cross-linkers, modified celluloses, hydroxypropylcellulose, hydroxymethylcellulose, dextrans, glycerin, metal salts, polyethyleneglycol, liquid crystals, rheological modifiers, modifiers of disjoining pressures, charged agents and non-charged agents, agents that modify the topography of mucous membrane systems, agents the lead to chemical and physical heterogeneity in mucous membrane systems, and combinations thereof.

DESCRIPTION OF THE FIGURES

FIG. 1 provides a depiction of a tear film.

DEFINITIONS

To facilitate an understanding of the invention set forth in the disclosure that follows, a number of terms are defined below.

The term mucous membrane refers broadly to the cellular covering exposed to the environment that lines the ocular, gastrointestinal, respiratory and urogenital systems. When using the term mucous membrane, we intentionally include the thin fluid films that are intimately associated with the cellular components and are responsible for wetting of the mucous membrane surface. Additionally, though not always used in this fashion, we include the cornea (that under normal conditions lacks mucous secreting cells) as a component of the mucous membrane of the ocular surface.

The term "dry eye disease (DED)" refers broadly to a family of conditions caused by inadequate secretion of the tear film or an increased loss of water from the tear film by evaporation.

The term "polymer multilayer" refers to the composition formed by sequential and repeated application of polymer(s) to form a multilayered structure. For example, polyelectrolyte multilayers are polymer multilayers formed by the alternating addition of anionic and cationic polyelectrolytes to a mucous membrane or support. The term "polymer multilayer" also refers to the composition formed by sequential and repeated application of polymer(s) to a mucous membrane or to a solid support. In addition, the term "polymer layer" can refer to a single layer composed of polymer molecules, such as anionic or cationic polyelectrolyte molecules, existing either as one layer within multiple layers, or as a single layer of only one type of polyelectrolyte molecules on a mucous membrane or support. While the delivery of the polymers to the mucous membrane or support is sequential in some preferred embodiments, the use of the term "polymer multilayer" is not limiting in terms of the resulting structure of the coating. It is well understood by those skilled in the art that inter-diffusion of polymers such as polyelectrolytes can take place leading to structures that may be well-mixed in terms of the distribution of anionic and cationic polyelectrolytes. It is also understood that the term polyelectrolyte includes polymer species as well as nanoparticulate species, and that it is not limiting in scope other than to indicate that the species possesses multiple charged or partially charged groups. It is also well understood by those skilled in the art that multilayer structures can be formed through a variety of interactions, including electrostatic interactions and others such as hydrogen bonding. These can also be formed through covalent reactions between polymers. Thus, the use of the term "polyelectrolyte" is not limiting in terms of the interactions leading to the formation of the mucous membrane constructs. Multilayers can be formed in situ on the surface or mucous membranes or pre-formed and subsequently transferred to the surface of mucous membranes. In other preferred embodiments of the invention, the polymer multilayers are preformed, and then transferred post-fabrication onto the mucous membrane.

The term "crosslinked" herein refers to a composition containing intermolecular crosslinks and optionally intramolecular crosslinks as well, arising from the formation of covalent bonds. Covalent bonding between two crosslinkable components may be direct, in which case an atom in one component is directly bound to an atom in the other component, or it may be indirect, through a linking group. A crosslinked structure may, in addition to covalent bonds, also include intermolecular and/or intramolecular noncovalent bonds such as hydrogen bonds and electrostatic (ionic) bonds.

The term "covalent modification agent" refers to any molecule that covalently links molecules to each other. Covalent modification agents include homobifunctional and heterobifunctional and multifunctional cross-linkers as well as photoactivatable cross linkers.

The term "homobifunctional cross-linker" refers to a molecule used to covalently link identical or similar molecules to each other. Homobifunctional cross-linkers have two identical reactive groups; thus, a homobifunctional cross-linker can only link molecules of the same type to each other. Conversely, a "heterobifunctional cross-linker" refers to a molecule used to covalently link dissimilar molecules to each other, because it has two or more different reactive groups that can interact with various molecules of different types. Hetero- and homo-multifunctional crosslinkers refers to multivalent crosslinkers with both hetero- and homo-crosslinking functionalities. Activated dendrimers are an example of multifunctional crosslinkers.

The term "subject" refers to any animal (e.g., a mammal), including, but not limited to, humans, non-human primates, rodents, dogs, cats, and the like, which is to be the recipient of a particular treatment. Typically, the terms "subject" and "patient" are used interchangeably herein. The term subject includes all vertebrates.

The term "surfactant" refers to an amphiphilic material that modifies the surface and interface properties of liquids or solids. Surfactants can reduce the surface tension between two liquids. Detergents, wetting agents, emulsifying agents, dispersion agents, and foam inhibitors are all surfactants.

The term "block copolymer" refers to a polymer consisting of at least two monomers. In a block copolymer, adjacent blocks are constitutionally different, i.e. adjacent blocks comprise constitutional units derived from different species of monomer or from the same species of monomer but with a different composition or sequence distribution of constitutional units. A block copolymer can be thought of as two homopolymers joined together at the ends.

The term "solvent" refers to a liquid that can dissolve a substance. The term "organic solvent" refers to a solvent derived from a petroleum-based product.

The term "polyelectrolyte" refers to a water-soluble macromolecular polymer substance containing many repeating ionic constituent units, including cations and anions.

The term "primary amine" refers to a derivative of ammonia in which a hydrogen has been replaced by a hydrocarbon unit. Primary amines have the general formula $RNH_2$ and examples include, but are not limited to, aniline, methylamine, and 1-propylamine.

The term "DNA delivery agent" refers to any molecule that can bring DNA into contact with an identified target. In some instances, a DNA delivery agent causes uptake of DNA into a cell or cells, in vitro or in vivo. DNA delivery agents can be viruses including, but not limited to, adenoviruses and retroviruses. DNA delivery agents can also be non-viral agents including, but not limited to, plasmids, lipids, liposomes, polymers and peptides.

The term "functionalized" refers to a modification of an existing molecular segment to generate or introduce a new reactive functional group (e.g., a maleimido or succinimidyl group) that is capable of undergoing reaction with another functional group (e.g., a sulfhydryl group) to form a covalent bond. For example, a component containing carboxylic acid (—COOH) groups can be functionalized by reaction with N-hydroxy-succinimide or N-hydroxysulfosuccinimide using known procedures, to form a new reactive functional group in the form of an activated carboxylate (which is a reactive electrophilic group), i.e., an N-hydroxysuccinimide ester or an N-hydroxysulfosuccinimide ester, respectively. In another example, carboxylic acid groups can be functionalized by reaction with an acyl halide, e.g., an acyl chloride, again using known procedures, to provide a new reactive functional group in the form of an anhydride.

As used herein, the term "aqueous solution" includes solutions, suspensions, dispersions, colloids, and the like containing water.

As used herein, the term "click chemistry" refers to the use of chemical building blocks with built-in high-energy content to drive a spontaneous and irreversible linkage reaction with appropriate complementary sites in other blocks. These chemical reactions (e.g., including, but not limited to, those between azide and acetylene groups that combine readily with each other) are specific and result in covalent linkage between the two molecules.

The term "native chemical ligation" refers to a chemoselective reaction of two unprotected peptide segments. The reaction results in an initial thioester-linked species, then spontaneous rearrangement of this transient intermediate occurs, yielding a full-length product with a native peptide bond at the ligation site.

The term "specific protein binding" refers to an interaction between two or more proteins that have high affinity and specificity for each other. Proteins must bind to specific other proteins in vivo in order to function. The proteins are required to bind to only one or a few other proteins of the few thousand proteins typically present in vivo; these interactions are employed in vitro in the present invention to attach agents to the target mucous membrane. In the context of the present invention, specific protein binding interactions include, but are not limited to, those between biotin and avidin, neutravidin, or streptavidin; glutathione-S-transferase and glutathione; and nickel-nitrilotriacetic acid and polyhistidine.

The term "device" refers to an object that contacts the body or bodily fluid of a subject for therapeutic or prophylactic purposes. Some devices may partially or indirectly contact the body or bodily fluid of a subject (e.g., catheter, dialysis tubing, diagnostic sensors, drug delivery devices), while other devices are completely imbedded in or encompassed by the body of a subject (e.g., stent, pacemaker, internally implanted defibrillator, angioplasty balloon, orthopedic device, spinal cage, implantable drug pump, artificial disc, ear disc).

The term "selective toxicity" refers to the property of differentially toxic effects on mammalian versus microbial cells. For example, a selectively toxic agent may effectively kill bacterial cells while permitting growth and viability of mammalian cells.

The term "toxic" refers to any detrimental or harmful effects on a subject, a cell, or a tissue as compared to the same cell or tissue prior to the administration of the toxicant.

As used herein, the terms "nanoparticle" and "nanoscale particles" are used interchangeably and refer to a nanoscale particle with a size that is measured in nanometers, for example, a nanoscopic particle that has at least one dimension of less than about 1000, 500, or 100 nm. Examples of nanoparticles include nanobeads, nanofibers, nanohorns, nano-onions, nanorods, and nanoropes.

As used herein, the term "microparticle", "beads" and "microscale particles" are used interchangeably and refers to a microscale particle with a size that is measured in micrometers, for example, a microscale particle that has at least one dimension of less than about 10 micrometers, 5 micrometers, or 2 micrometers.

DETAILED DESCRIPTION OF THE INVENTION

The present invention relates to methods and compositions for modifying mucous membranes. In particular, the present invention relates to treating diseases associated with mucous membranes by changing the intrinsic chemical composition, viscoelasticity and/or physical features of a target mucous membrane. The alteration of the mucous membrane can result in improved interaction with the native thin films (e.g. tear film, saliva, vaginal secretions, gastrointestinal thin films, respiratory thin films) such that a clinical benefit is obtained and can also prepare the cellular surface of the mucous membrane to optimally interact with topical agents specifically chosen to interact with the "engineered" surface of the mucous membrane to improve mucous membrane/ocular surface health. Here the mucous membrane includes but is not limited to cellular, mucous, aqueous and lipid components. The present invention provides for engineering of the tear film to address changes in tear film stability and breakup that result from inflammation of the ocular surface and mucous membrane system.

The compositions and systems of the present invention find use in treating a wide variety of conditions and diseases associated with mucous membranes. In some preferred embodiments, the treatments are palliative and relieve symptoms associated with the disease. In preferred embodiments, treatment with the compositions and systems of the present invention relieve pain, discomfort, stress or suffering of a patient through physical modification of one or more target mucous membranes in the patient. Disease and conditions that may be treated with the compositions and systems of the present invention include, dry eye disorders (attributable to a large number of underlying causes), dry mouth, Sjogrens syndrome, complications of Stevens Johnson disease, Aphthous stomatitis, Behcet syndrome, viral infections (e.g., herpes simplex virus infections, herpes varicella-zoster virus infections, Epstein-Bar virus infection, cytomegalovirus infection, hand, foot and mouth disease, herpangina, Vesiculobullous diseases (e.g., pemphigus, pemphigoid, erythema multiforme), lesions associated with hyperkeratosis (e.g., leukoplakia, lichen planus, lupus erythematosus, white sponge nevus, hairy tongue, actinic cheilitis), Precancerous lesions (e.g., erythroplakia, Bowen's disease, chronic lip diseases, papillomas, ulcerations, pigmented lesions), Atrophic stomatitis, Burning Mouth Syndrome, Oral candidiasis, Median rhomboid glossitis, Angular cheilitis, and oral manifestations of systemic diseases (e.g., orofacial granulomatosis, Crohn's disease, Wegener's granulomatosis, Langerhans histiocytoses), Barrett's esophagus (columnar epithelial lined oesophagus-CELLO), gastric ulceration, dry nasal passages arising from myriad causes, cystic fibrosis, respiratory distress syndrome of premature infants, vaginal dryness and vaginal irritation. In some embodiments, the present invention provides methods to prevent disease that has not yet formed.

The tear film serves several purposes. It keeps the eye moist, creates a smooth surface for light to pass through the eye, nourishes the front of the eye, and provides protection from injury and infection.

Ocular surface diseases can result from a variety of causes, including dysregulation of the tear film, trauma, toxicity, inflammation, metabolic disorders (e.g. diabetes), neural dysregulation (e.g., neuroparalytic keratitis, neurotrophic keratitis) inadequate functioning of the lids (e.g., cranial nerve VII palsy, lagophthalmos, exposure keratopathy), maladaptive relationship between the globe position relative to the lids and orbital contexts (e.g. exophthalmos; enophthalmos); complications of contact lens wear; toxic events (alkali burn; acid burn; radiation, solar keratitis, envenomation by invertebrates and vertebrates), exposure to particulates, urticating hairs of invertebrates (tarantulas and caterpillars associated with ophthalmia nodosa), infection (e.g. viral, fungal, parasitic, bacterial) and inflammatory disorders of diverse origin.

Ocular surface disorders associated with the tear film can be due to dysregulated production of the tear film constituents or due to abnormal mechanical distribution of the tear film (e.g. associated with lid dysfunction or due to an inability of the lids to adequately cover the globe). An extensive review emerging from an international dry eye disease workshop was published in 2007. The Ocular Surface/April 2007, Vol. 5, No. 2; theocularsurface.com, 2007 Report of the International Dry Eye WorkShop (DEWS) Tear film disorders can be broadly grouped into deficiencies in the production of the aqueous component (keratoconjunctivitis sicca or KCS) and into "qualitative" disorders of other constituents due to inadequate production or dysregulated composition. Xerophthalmia is a term that usually implies a destructive dryness of the conjunctival epithelium due to dietary vitamin A deficiency—a rare condition in developed countries, but still causing much damage in developing countries. Other forms of dry eye are associated with aging, poor lid closure, scarring from previous injury, or autoimmune diseases exemplified by but not limited to rheumatoid arthritis and Sjogren's syndrome.

In aqueous deficient dry eye disease the aqueous tear layer is affected, resulting in aqueous tear deficiency (ATD) or lacrimal hyposecretion. The lacrimal gland does not produce sufficient tears to keep the entire conjunctiva and cornea covered by a complete layer. This usually occurs in people who are otherwise healthy. Increased age (especially in post menopausal women) is associated with decreased tearing.

Causes include idiopathic, congenital alacrima, xerophthalmia, lacrimal gland ablation, and sensory denervation. In rare cases, it may be a symptom of collagen vascular diseases, including rheumatoid arthritis, Wegener's granulomatosis, and systemic lupus erythematosus. Sjögren's syndrome and autoimmune diseases associated with Sjögren's syndrome are also conditions associated with aqueous tear deficiency. Thyroid disease and alterations in nerve growth factor have also been implicated. Numerous drugs including but not limited to isotretinoin, sedatives, diuretics, tricyclic antidepressants, antihypertensives, oral contraceptives, antihistamines, nasal decongestants, beta-blockers, phenothiazines, atropine, and pain relieving opiates such as morphine can cause or worsen this condition. Infiltration of the lacrimal glands by sarcoidosis or tumors, or postradiation fibrosis of the lacrimal glands can also cause this condition. Additionally, disruption of the innervation to the lacrimal gland, trauma, toxic degeneration of lacrimal tissue, goblet cells and/or Meibomian glands due to thermal damage (e.g., burns) as well as exposure to radiation and cytotoxins can lead to decreased production of essential constituents of the tear film.

Tear film disorders can be associated with but are not limited to inadequate secretion or altered composition of any of the elements of tear film. In other words, sometimes the eye does not produce enough tears. Other times, the tears that the eye produces are not "healthy." This change of the tear film composition results in irritation and changes on the eye surface that lead to characteristic symptoms, such as a foreign body sensation, sandy or burning sensation, discomfort, blurred vision, and redness of the eye that can progress as the day goes on. Decreased tear production associated with dry eye disease may be caused by any condition that decreases sensation of the cornea (the transparent membrane covering the iris and pupil) or damages the tear glands, called lacrimal and accessory lacrimal glands. As corneal sensation is part of the tear-making response, eyes with decreased sensation will tear less. Some of the causes of decreased corneal sensation include long-term contact lens wear, diabetes, nerve damage associated with tumors and surgery and certain viral infections. A common cause of damage to the lacrimal gland is Sjogren's syndrome, a chronic inflammatory disease in which mucous membranes, especially those in the eyes and the mouth, become extremely dry. Primary Sjogren's occurs alone with no other associated disorders, while secondary Sjogren's is often accompanied by other autoimmune disorders such as lupus or rheumatoid arthritis.

Ocular surface disease can also result from deficiencies in the amount and/or composition of the mucin and/or lipid constituents of the tear film. For example, Mebomian glands (also referred to as tarsal glands) located in the lid margins are largely responsible for secretion of the lipid constituents of the tear film. Increased evaporation of the water from the tear film can increase due to inadequate production and or malcomposition of the lipid constituents associated with these glands. This has led to use of the term Meibomian gland dysfunction (MGD) as a significant factor in the development of dry eye diseases (DEDs). Blepharitis (inflammation of the eyelid), decreases production and/or quality of the secretions by the Meibomian glands of the eyelids that can lead to increased evaporative loss of the aqueous component and contribute to instability of the tear film. The complexity and importance of Meibomian gland function to ocular surface health has been recently reviewed. The International Workshop on Meibomian Gland Dysfunction: Executive Summary; Nichols et al., Invest. Ophthalmol. Vis. Sci. Mar. 30, 2011 vol. 52 no. 4 1922-1929.

Similarly, mucins are essential to maintaining ocular surface health. Consisting of both soluble and membrane-bound molecules, ocular surface mucins are highly glycosylated proteins that help structure the tear film by binding both to each other and to the aqueous component of the tear film. By helping to stabilize the tear film, mucins are essential for maintaining ocular surface health. In a normal eye, the concentration of ocular surface mucins is highest near the surface of the globe, and it gradually decreases as the tear/air interface is approached.

Secreted mucins—such as MUC4 and MUC7—are produced by the lacrimal gland. These are the smallest mucin molecules in the tear film.
  Gel-forming mucins—such as MUC5-AC—are secreted by the goblet cells of the conjunctiva. Like the secreted mucins, gel-forming mucins are dissolved in the tear film, but gel-forming mucins are larger and more interactive with other mucin molecules.
  Membrane-associated mucins—such as MUC1 and MUC16—are even longer molecules that have an intracellular extension that anchors them to epithelial cells. These mucins play a key role in protecting the ocular surface, and when these mucins are absent or damaged, ocular surface staining results. Inflammatory processes can eradicate mucin-producing cells, and because inflammation typically plays a significant role in dry eye disease, long-term exposure to inflammatory mediators could damage mucin-producing cells and significantly impair normal mucin function.

Supporting the importance of mucins is a recent study that investigated a specific mucin, MUC5AC, the most abundant gel-forming mucin in the ocular system. However, the specific function is unknown. In a recent study, a Muc5ac knockout (KO) mouse model was subjected to various physiological measurements as compared to its wide-type (WT) control. When KO mice were compared to WT mice, the mean tear break up time (TBUT) values were significantly lower and corneal fluorescein staining scores were significantly higher. But the tear volume was not changed. These results document a significant difference in the quality, but not the quantity, of tear fluid in the KO mice compared to WT mice. Other studies have suggested the importance of mucin glycosylation to maintenance of ocular surface health. Yukitaka et al., Invest Ophthalmol Vis Sci. 1998; 39:2602-2609. Mucin deficiency also occurs in association with hypovitaminosis A. These studies along with many others document the importance of tear composition and not just volume in maintaining ocular surface health. Floyd et al., PLoS One. 2012; 7(12):e50704. doi: 10.1371/journal.pone.0050704. Epub 2012 Dec. 18.

The entire gastrointestinal system is lined by epithelium and an associated thin fluid film coating essential to maintenance of mucosal barrier function. In the following a focused concise review of the oralpharyngeal region and associated salivary secretions is presented. This is to serve simply as a nonexclusionary exemplar of the myriad functions and importance of the thin film coatings of the alimentary tract. At all locations along the alimentary tract complex thin film coatings are associated with the epithelial lining. These thin film coatings possess lipids, mucins, proteins and aqueous constituents and are essential for maintaining mucosal barrier function and participate in the unique functionality associated with each discrete alimentary region. A variety of inflammatory, infectious, genetic, age-related, hormonal, metabolic, immune mediated, idiopathic and neoplastic conditions as well as extrinsic factors including but not limited to drugs, surgical interventions, trauma, exposure to toxins (e.g. tobacco, alcohol, environmental toxins) and therapeutic interventions such as chemotherapy and radiation therapy can compromise the integrity of the mucosa and its associated thin films at any point along the alimentary system.

The oral epithelium together with the saliva and its components forms a complex structure which is the first line of defense in the oral cavity. The surface of superficial cells of the oral epithelium contains ridge-like folds, microplicae (MPL), which are typical of the surfaces of areas covered with protective mucus. A knowledge gap exists concerning the exact functions of the MPL. The salivary mucus gel performs a protective diffusion membrane against harmful substances and this membrane is built up by epithelial cells covered by a highly hydrated and viscous gel, where mucins constitute the scaffold. The interaction between the MPL-structure and the mucins is shown in cornea, so that mucins are expressed on the tips of the MPL of the epithelial cells. The salivary mucous barrier is required to protect the superficial cells and the MPL-structure together with membrane anchored mucin binding protein (MBP) is thought to form the ground to this mucous barrier.

Saliva provides the fluid constituents that interact with the surface of the mucosal membrane that lines the oral cavity. Like tears it is complex in its composition and has many additional roles associated with the digestive process. Histatins are polypeptides which possess exceptional anti-fungal and anti-bacterial activities, but are nevertheless present only in saliva. Proline-rich proteins (PRPs) are members of a closely related family, of which the acidic PRPs are found solely in saliva, whereas the basic PRPs are also found in other secretions. Mucins are a group of glycoproteins that contribute to the visco-elastic character of the mucosal secretions. Despite the similarities in their structure and behavior, mucins have distinct tissue distributions and amino acid sequences. Other salivary proteins are present in one or more mucosal secretions. Lysozyme is an example of a component belonging to an ancient self-defense system, whereas secretory immunoglobulin A (sIgA) is the secreted part of a sophisticated adaptive immune system. Cystatins are closely related proteins which belong to a multigene family. Alpha-Amylase is a component that is believed to play a specific role in digestion, but is nevertheless present in several body fluids. Kallikrein and albumin are components of blood plasma. But whereas albumin diffuses into the different mucosal secretions, kallikrein is secreted specifically by the mucosal glands.

Drying of the mucous membranes of the oral cavity (dry mouth) is also a common clinical condition with a plethora of underlying causes. Symptoms of dry mouth include: Sensation of dryness; Saliva that seems thick and stringy; Sores or split skin at the corners of the mouth; Cracked lips; Bad breath; Difficulty speaking and swallowing; Sore throat; Altered sense of taste; Fungal infection; and Increased plaque, tooth decay and gum disease. A brief non-limiting list of underlying causes includes: Medications. Hundreds of medications, including some over-the-counter drugs, produce dry mouth as a side effect. Among the more likely types to cause problems are some of the drugs used to treat depression and anxiety, antihistamines, decongestants, high blood pressure medications, anti-diarrheals, muscle relaxants, drugs for urinary incontinence, and Parkinson's disease medications. Aging. Getting older isn't a risk factor for dry mouth on its own; however, older people are more likely to be taking medications that may cause dry mouth. Also, older people are more likely to have other health conditions that may cause dry mouth. Cancer therapy. Chemotherapy drugs can change the nature of saliva and the amount produced. Radiation treatments to the head and neck can damage salivary glands, causing a marked decrease in saliva production. Nerve damage. An injury or surgery that causes nerve damage to the head and neck area also can result in xerostomia. Other health conditions. Dry mouth can be a consequence of certain health conditions—or their treatments—including the autoimmune disease Sjogren's syndrome, diabetes, Parkinson's disease, HIV/AIDS, anxiety disorders and depression. Stroke and Alzheimer's disease may cause a perception of dry mouth, even though the salivary glands are functioning normally. Cancer of the salivary glands and surgical removal of the salivary glands. Snoring and breathing with the mouth open also can contribute to the problem. Tobacco use. Smoking or chewing tobacco can increase dry mouth symptoms.

Similar to dry eye diseases, the underlying deficiencies in wetting of the oral mucous membranes can be associated with a deficiency in the aqueous phase of saliva but alterations in mucin amount and composition has also been suggested to play a possible role.

Water content of saliva depends of acetylcholine levels, glandular innervation, M3R signaling, calcium tunneling and water release, among other factors. However, unstimulated salivary flow correlates only poorly with symptoms of mouth dryness. Salivary mucins are glycoproteins characterized by the presence of large oligosaccharide side chains attached to the protein backbone. These molecules are key saliva components that are required to sequester water and thereby moisturize, as well as lubricate the oral mucosa. In the labial salivary glands of SS patients, morphological and functional alterations are detectable that affect the maturation and trafficking of salivary mucins.

The reproductive system is covered by a mucosal membrane and shares in common with all mucosa, cellular elements that have an intimate association with thin fluid films that are complex in nature. These thin fluid films are an essential element for maintenance of the mucosal barrier function and are essential for normal reproductive processes providing not only lubrication but also engaged in fertilization and implantation. Here we present a very brief description of the importance of cericovaginal fluids (CVF) as a nonexclusive exemplar of the reproductive tract in general. CVF is comprised of fluid originating from the vagina, as well as other fluids flowing into the vagina, such as cervical mucus and endometrial and oviductal fluids. Vaginal dryness is a common problem for women during and after menopause, although inadequate vaginal lubrication can occur at any age. Vaginal dryness is a hallmark sign of vaginal atrophy (atrophic vaginitis)—thinning and inflammation of the vaginal walls due to a decline in estrogen. Similar to other mucous membranes the vaginal vault has complex thin films associated with its cellular surface composed of a variety of mucins, proteins, electrolytes, lipids and water. Cervicovaginal fluid is complex and arises from glands as well as cellular elements. It varies in composition and amount and is affected by numerous factors exemplified by but not limited to age, stage in the estrous cycle, menopause, sexual arousal, a host of drugs, relative state of health/disease, exposure to radiation and the like.

Similar to all of the previous examples, the thin films that coat the respiratory tract epithelium are of central importance to normal functioning and maintaining the health of the lining and function of the respiratory system. The respiratory system is composed of the nasal passages, trachea, bronchi and all components of the lungs. Like all other thin films intimately associated with mucosal surfaces the thin fluid films are complex with many constituents including but not limited to aqueous, proteins (including antimicrobial peptides), lipid, mucins and electrolytes. The exact composition in healthy subjects varies depending on anatomic location (e.g. nasal passages, trachea, bronchi, bronchiole, alveoli). These have myriad functions including maintenance of the mucosal barrier, maintenance of acid-base balance, innate immunity and altering surface tension (through surfactants) for normal respiratory function. Native small airways must remain wet enough to be pliable and support ciliary clearance, but dry enough to remain patent for gas flow. The airway epithelial lining must both absorb and secrete ions to maintain a critical level of fluid on its surface. Lack of appropriate maturity of the fluid film or disturbances in the amount and/or composition of thin fluid films can result from myriad causes including premature birth, genetic defects (e.g. cystic fibrosis), chronic obstructive pulmonary disease, dehydrating environments, chronic inflammatory diseases, infectious agents (bacterial, fungal, viral, *mycoplasma, chlamydia*) exposure to environmental toxins, tobacco use, neoplastic disorders, drugs, ionizing radiation and idiopathic causes. These can all lead to discomfort, impaired respiratory function and inadequate oxygenation of the individual so affected.

Three clinical conditions are presented here in the context of the invention: cystic fibrosis, dry nasal passages and infant respiratory distress syndrome. These are to serve as non-limiting exemplars of the clinical conditions that are addressable with use of the invention.

1. Cystic Fibrosis: A defect in the CFTR gene causes cystic fibrosis (CF). This gene makes a protein that controls the movement of salt and water in and out of your body's cells. In people who have CF, the gene makes a protein that doesn't work well. This causes thick, sticky mucus and very salty sweat. The excessive buildup of mucus makes it easy for bacteria to grow. This leads to repeated, serious lung infections. Over time, these infections can severely damage your lungs. Additionally, the mucus buildup can be so severe that it blocks air passages compromising breathing. Excessive mucus buildup can also occur in chronic obstructive pulmonary disease (COPD) and in chronic bronchitis. Treatments that decreased mucoadhesion to the cellular constituents of the airway would assist in mobilizing mucus along the respiratory tract and decrease buildup of mucus with associated development of respiratory impairment due to impairment of airflow and the development of infections.

2. Dry Nasal Passages. Dry nose is a common condition that can arise from myriad underlying causes with non-limiting examples including arid environmental conditions (affected by geographic locale as well as a decrease in relative humidity in association with air conditioning/heating of home environment), as a side effect of numerous medications, in association with autoimmune diseases exemplified by but not limited to Sjogren's disease and in association with dry eye (keratoconjunctivitis sicca of diverse underlying causes). Regardless of the underlying cause, an improved palliative approach to improve the quality and duration of moistening of the nasal mucosa would improve patient comfort.

3. Infant respiratory distress syndrome (RDS; also known as hyaline membrane disease): RDS is a common lung disorder in premature infants. In fact, many infants born before 28 weeks of pregnancy develop RDS. It is diagnosed by identification of severe respiratory distress lasting more than 48 hrs after birth or rapid response to surfactant treatment. Relevant information regarding RDS in the US includes: 4.3 million annual births; 12.5% are premature=537,500 infant/yr; 1.5% are <1500 grams~30 weeks=~65,000VLBW infants of whom 80% have RDS RDS in almost ⅓ in infants>30<36 weeks~157,500 infants; or 222,500 total infants/year consuming $2.0 billion dollars of health resources annually.

Surfactant production is gestational stage dependent increasing near the normal delivery time. Surfactants play multiple roles including serving to minimize infection as well as decrease surface tension within alveoli facilitating normal respiration. Surfactant: Prevents atelectasis, edema; Decreases shear forces and volume trauma; Prevents airway closure; and Required for post-natal gas exchange RDS might be an early phase of bronchopulmonary dysplasia (BPD). This is another breathing disorder that affects premature babies. RDS usually develops in the first 24 hours after birth. If premature infants still have breathing problems by the time they reach their original due dates, they may be diagnosed with BPD. Some of the life-saving treatments used for RDS may cause BPD. The main cause of respiratory distress syndrome (RDS) is a lack of surfactant in the lungs. Surfactant is a liquid that coats the inside of the lungs. A fetus's lungs start making surfactant during the third trimester of pregnancy (weeks 26 through labor and delivery). The substance coats the insides of the air sacs in the lungs and decreases surface tension of the respiratory surface facilitating expansion and contraction throughout the breathing cycle. This helps keep the lungs open so breathing can occur after birth. Without enough surfactant, the lungs will likely collapse when the infant exhales (breathes out). The infant then has to work harder to breathe. He or she might not be able to get enough oxygen to support the body's organs. Some full-term infants develop RDS because they have faulty genes that affect how their bodies make surfactant.

Treatment: Treatment for respiratory distress syndrome (RDS) usually begins as soon as an infant is born, sometimes in the delivery room. Most infants who show signs of RDS are quickly moved to a neonatal intensive care unit (NICU). There they receive around-the-clock treatment from health care professionals who specialize in treating premature infants. The most important treatments for RDS are surfactant replacement therapy with breathing support from a ventilator or nasal continuous positive airway pressure (NCPAP) machine and oxygen therapy.

Surfactant Replacement Therapy: Surfactant is a liquid that coats the inside of the lungs. It helps keep them open so that an infant can breathe in air once he or she is born. Babies who have RDS are given surfactant until their lungs are able to start making the substance on their own. Surfactant usually is given through a breathing tube. The tube allows the surfactant to go directly into the baby's lungs. Once the surfactant is given, the breathing tube is connected to a ventilator, or the baby may get breathing support from NCPAP. Surfactant often is given right after birth in the delivery room to try to prevent or treat RDS. It also may be given several times in the days that follow, until the baby is able to breathe better. Some women are given medicines called corticosteroids during pregnancy. These medicines can speed up surfactant production and lung development in a fetus. Even if you had these medicines, an infant may still need surfactant replacement therapy after birth.

Surfactants administered are typically of animal origin (e.g., Curosurf is of porcine origin; SURVANTA® (beractant) is of bovine origin). In RDS infants, surfactant may be administered multiple times and as close as every 6 hours with initial treatment in conjunction with assisted ventilation. Retreatment is common in the treatment of this condition. Treatment with surfactant requires intubation, instillation of the surfactant and then being placed on a ventilator. Retreatment is common and initiation is based on response to treatment with nuances in decision making being health care facility dependent. There are many possible causes for needing re-treatment including proteolytic degradation of the exogenously applied surfactant, relative inability of infant to produce own surfactant, inadequate distribution with initial dose, mobilization of surfactant off of the alveolar surface; among many others.

The present invention allows for increased effectiveness of these therapies, decreases required time on the ventilator, and decreases the number of required re-treatment (i.e., increase time period of durable effect through stabilizing presence at alveolar surface, minimizing inactivation (free radicals, proteases, phospholipases) and/or inhibition of activity (serum proteins, lipids & amino acids).

Accordingly, in some embodiments, the present invention provides compositions for modifying a mucous membrane comprising a first agent that physically interacts or reacts with one or more components of said mucous membrane using a physiologically acceptable carrier. In some preferred embodiments, the physiologically acceptable carrier is compatible with the function of a mucous membrane. The present invention is not limited to modification of any particular mucous membrane. Suitable, non-limiting examples of mucous membranes include the ocular surface (cornea, bulbar conjunctiva, palpebral conjunctiva and lid margin), oral mucous membranes (including pharyngeal structures), vaginal, cervical and other mucous membranes of the female reproductive tract, nasal mucous membranes, respiratory mucous membranes including trachea, bronchi, bronchioles and alveoli, and gastrointestinal mucous membranes (including esophageal membranes). In particularly preferred embodiments, the mucous membranes are the ocular surface. The invention may alter the surface chemistry and or biophysical attributes of the cell surface that comprise the mucous membranes or may alter the chemistry and/or biophysical attributes of the thin films intimately associated with said cellular constituents. The present invention is not limited to the modification of any particular component of the mucous membranes. Suitable targets for modification by the compositions and methods of the present invention include, but are not limited to, lipid, protein, glycoaminoglycan, and/or carbohydrate components of cell surfaces and/or the tear film or other intimately associated thin films associated with mucous membranes (e.g., saliva, thin films associated with the alimentary tract, cervicovaginal secretions and thin films associated with the female reproductive tract, respiratory thin films). The present invention contemplates modification of mucous membranes in a variety of different subjects, including, but not limited to, humans, companion animals such as dogs and cats, and stock animals (horses, cattle, pigs, goats, sheep, horses, mules, donkeys) and exotic animals (birds, fish, reptiles amphibians and exotic mammals).

In preferred embodiments, the compositions and methods of the present invention utilize an agent that modifies a mucous membrane by physical interaction or reaction with one or more components of the mucous membrane and/or intimately associated thin films.

Exemplary physical interactions generally include, but are not limited to, non-covalent binding to the component or components of the mucous membrane as well as general physical interactions such as those mediated by differences in charge, capacity to hydrogen bond, interact via pi-pi interactions or van der Waals forces or physiochemical properties such as hydrophobicity or hydrophilicity. In some cases, the physical interactions will be mediated by the aqueous, lipid, protein, carbohydrate or the mucin constituents of the cellular and/or thin film elements of the mucous membranes. In some embodiments, the compositions as described herein are deposited on a mucous membrane (cellular and/or thin fluid films) by electrostatic bonding. In other embodiments, non-electrostatic interactions are utilized, such as van der Waals interactions, metal ion-ligand coordination or hydrogen bonding. Hydrophobic interactions can also be used. In some embodiments, the compositions as described herein are deposited by piezoelectric application, using methods and systems as described in, for example, U.S. Pat. No. 6,368,079 and Sumerel et al., 2006, Biotechnol. J. 1:976-987. In other embodiments, the compositions are directly or indirectly deposited onto the target mucous membrane by using electrojetting technologies, including electroextrusion, electrospraying and electrospinning. In other embodiments, the compositions are directly or indirectly deposited by the placement of a droplet, cream, ointment or aerosolized spray of material into the eye or mucous membrane-containing system. Other still other embodiments, the compositions are delivered to the mucous membrane system using a patch, including in some embodiment a patch that can be in the form of a contact lens or similar geometry. In embodiments aimed at modifying the mucous membranes of the oral cavity, esophagus or other components of the alimentary system liquid rinses or swallowable formulations are used. In embodiments aimed at coating the nasal cavity aerosol sprays, nebulizers, or vaporizers are used. For delivery of material to the lung alveoli, liquid formulations (solutions/suspensions) and/or nebulizers/vaporizers can be used. The compositions may be released as a spike of material or they may be released from such delivery systems in a sustained manner over a desired duration. The non-covalent binding may be specific or non-specific in nature. If more than one agent is utilized to modify the mucous membrane, including the cellular and/or thin film elements of the mucous membrane, the agents may be added at the same time or sequentially. In some embodiments, the one or more agents may be applied to form a layered structure. For example, a first agent or agent may be applied to the mucous membrane to form a modified mucous membrane and then additional agent(s) are applied to the modified mucous membrane. In certain other embodiments the agents can be released sequentially from a single formulation with differing release kinetics using controlled release formulation designs. The additional agents may physically interact with either the first agent, components of the mucous membrane, or both. In other embodiments, the agents or agents may be applied in patterns, including random patterns, or gradients on the target mucous membrane. In some embodiments, the compositions are deposited as layers. In some embodiments, layered deposition is sequential. In some embodiments, deposition is simultaneous. In some embodiments polyelectrolyte multilayers are formed in situ or transferred to the mucous membrane being treated.

Exemplary physical and/or chemical reactions generally include covalent modification of one or more components of the mucous membranes. Covalent modification is typically mediated by the reaction of an active functional group with a chemical moiety present one or more components of the mucous membrane. Suitable target groups for covalent modification include, but are not limited to carboxy, thiol, hydroxyl, amine and sugar groups. These groups are preferably present on one or more components of the target mucous membrane. The covalent modification may be direct in which the first agent is directly attached to the component of the mucous membrane or indirect in which the first agent is attached via a linker or other moiety that is first reacted with one or more components of the mucous membrane and then which is in turn reacted with one or more agents as desired. In some embodiments, the target mucous membrane is modified with one or more agents by contacting the mucous membrane with one or more functionalized agents containing a functional group that forms a covalent bond with one or more target chemical moieties on one or more components of the mucous membrane. The one or more agents may be added at the same time or sequentially. In other embodiments, the target mucous membrane may be modified with one or more agents by first functionalizing one or more components of the mucous membrane and then adding one or more agents to the functionalized mucous membrane to produce a modified mucous membrane with the one or more agents covalently attached thereto. The site of action of the functionalizing agents on the mucous membrane is not limited by this invention, and in some embodiments the one or multiple functionalizing agents may interact with different components of the mucous membrane. The one or more agents may be added at the same time or sequentially. In some embodiments, the one or more agents may be applied to form a layered structure. In other embodiments, the agents or agents may be applied in patterns or gradients on the target mucous membrane.

It will be further understood that target mucous membranes may be modified by a combination of agents that physically interact with components of the mucous membrane and optionally agent(s) that physically react with the mucous membrane following an initial modification. Physical interactions may involve, but are not limited to, van der Waals forces, hydrogen bonding, electrostatic interactions, metal ion-ligand coordination interactions, dispersion forces, London interactions and combinations thereof. For example, the target mucous membrane may first be treated with an agent or agents that physically interact with the mucous membrane and then the modified mucous membrane is treated with an agent or agents that physically react with either mucous membrane components or the first agent or agents. Likewise, the target mucous membrane may first be treated with an agent or agents that physically reacts with the mucous membrane and then the modified mucous membrane is treated with an agent or agents that physically interacts with either mucous membrane components or the first agent or agents.

A wide variety of agents may be used to modify target mucous membranes. Suitable agents include, but are not limited to reducing agents, oxidizing agents, homobifunctional linkers, heterobifunctional linkers, organic molecules comprising a reactive group, organic molecules comprising a click chemistry functionality, organic molecules comprising a photoactivatable group, agents that bind to one or more lipids, carbohydrates, glycoaminoglycans and proteins, and sensitizing agents. Suitable agents also include polymers, surfactants, polyelectrolytes, dendrimers, micro and nanoparticles and beads of inorganic or organic materials. The suitable agents may also be electrically neutral or salts of organic or inorganic compositions. Suitable agents also includes reducing agents, for example, TCEP, ascorbic acid, anglutathione, and dithiothreitol.

In some embodiments, the first agent is or comprises a homobifunctional linker. The present invention is not limited to the use of any particular homobifunctional linkers. Suitable homobifunctional linkers include, but are not limited to N-hydroxysuccinimidyl ester (e.g., including, but not limited to, disuccinimidyl ester, dithiobis(succinimidylpropionate), 3,3'-dithiobis(sulfosuccinimidylpropionate), disuccinimidyl suberate, bis(sulfosuccinimidyl)suberate, disuccinimidyl tartarate, disulfosuccinimidyl tartarate, bis[2-(succinimidyloxycarbonyloxy)ethyllsulfone, bis[2-(sulfosuccinimidooxycarbonyloxy)ethyllsulfone, ethylene glycolbis(succinimidylsuccinate), ethylene glycolbis(sulfosuccinimidylsuccinate), disuccinimidyl glutarate, and N,N'-disuccinimidylcarbonate). In some embodiments, the homobifunctional linker is at a concentration between 1 nanomolar and 100 millimolar. In some preferred embodiments, the homobifunctional linker is at a concentration between 10 micromolar and 1 millimolar.

In some embodiments, the first agent is or comprises a heterobifunctional linker. The present invention is not limited to the use of any particular heterobifunctional linkers. Suitable heterobifunctional linkers include, but are not limited to, N-succinimidyl 3-(2-pyridyldithio)propionate, succinimidyl 6-(3-[2-pyridyldithiol-propionamido)hexanoate, sulfosuccinimidyl 6-(3'-[2-pyridyldithiol-propionamido)hexanoate, succinimidyloxycarbonyl-α-methyl-α-(2-pyridyldithio)toluene, sulfosuccinimidyl-6-[α-methyl-α-(2-pyridyldithio)toluamidolhexanoate, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxy-sulfosuccinimide ester, N-succinimidyl(4-iodoacetyl)aminobenzoate, sulfo-succinimidyl(4-iodoacetyl)aminobenzoate, succinimidyl-4-(p-maleimidophenyl)butyrate, sulfosuccinimidyl-4-(p-maleimidophenyl)butyrate, N-(γ-maleimidobutyryloxy)succinimide ester, N-(γ-maleimidobutyryloxy)sulfosuccinimide ester, succinimidyl 6-((iodoacetyl)amino)hexanoate, succinimidyl 6-(6-(((4-iodoacetyl)amino)hexanoyl)amino)hexanoate, succinimidyl 4-(((iodoacetyl)amino)methyl)cyclohexane-1-carboxylate, succinimidyl 6-(((4-iodoacetyl)amino)methyl)cyclohexane-1-carbonyl)amino)-hexanoate, and p-nitrophenyl iodoacetate. In some embodiments, the heterobifunctional linker is modified with functional groups, rendering it soluble in aqueous solvents for delivery as an aqueous solution. Furthermore, in some embodiments, the aqueous solution contains additives (e.g., including, but not limited to, surfactants and block copolymers). In other embodiments, a multiplicity of hetero-bifunctional cross-linkers can be attached to a molecule, polymer or particle to serve as the linking agent. In other embodiments, the heterobifunctional cross-linker is dissolved in an organic solvent (e.g., including, but not limited to, dimethyl sulfoxide).

In some embodiments, the agent is or comprises an organic molecule comprising a reactive group. Suitable organic molecules include but are not limited to amino acids, peptides, polypeptides, proteins, lipids, carbohydrates, glycoaminoglycans, nucleic acids and combinations thereof. The organic molecules may either naturally comprise or be modified to comprise a reactive group. In some embodiments, the organic molecules comprising a reactive group are modified with one or more homobifunctional and/or heterobifunctional linkers as described above. These modified organic molecules are thus functionalized with one or more reactive groups and can be applied to the target mucous membrane to provide a modified mucous membrane. The suitable organic molecules can be naturally occurring or synthetic in nature, and can include polymers, beads, nano and microparticles, and amphiphilic molecules.

In some embodiments, the agent is or comprises an organic molecule comprising a click chemistry functionality. Suitable organic molecules include but are not limited to amino acids, peptides, polypeptides, proteins, lipids, carbohydrates, glycoaminoglycans, nucleic acids and combinations thereof. The suitable organic molecules can be naturally occurring or synthetic in nature, and can include polymers, beads, nano and microparticles, and amphiphilic molecules. The organic molecules are preferably modified to comprise a click chemistry functionality. In some preferred embodiments, the target mucous membrane is first treated with linkers (e.g., homobifunctional or heterobifunctional linkers) comprising either an azide group or an alkyne group so that suitable click chemistries can be utilized. For example, in some embodiments, a linker comprising an activated acid (e.g., NHS (N-hydroxysuccinimydl)) is used to react with amine groups presented by components of the mucous membrane and a second linker comprising a maleimide is used to react with sulfhydryl groups presented by components of the mucous membrane. In some embodiments, the malimide and activated acid are conjugated to an alkyne. From this point, widely available click chemistries can be used to add desired agents to the modified surface of the mucous membrane. In some embodiments, the agent is an azide conjugate or otherwise comprises an azide group and is reacted with the alkyne groups displayed on the mucous membrane in a Huisgen Cycloaddition.

In some embodiments, the agent is or comprises a photoactivatable group or linker. Suitable photoactivatable linkers include, but are not limited to, aryl azide N-((2-pyridyldithio)ethyl)-4-azidosalicylamide, 4-azido-2,3,5,6-tetrafluorobenzoic acid, succinimidyl ester, 4-azido-2,3,5,6-tetrafluorobenzoic acid, STP ester, benzophenone maleimide, succinimidyl ester of 4-benzoylbenzoic acid, N-5-Azido-2-Nitrobenzoyloxysuccinimide, N-Hydroxysulfosuccinimidyl-4-azidobenzoate, N-Hydroxysuccinimidyl-4-azidosalicylic acid, and (4[p-Azidosalicylamidolbutylamine). In some embodiments, the target mucous membrane is first modified with a linker comprising the photoactivatable group. The groups are then activated either in the presence of desired agent or a desired agent is added following photoactivation to provide a modified mucous membrane. Suitable desired agents in these embodiments include, but are not limited to, amino acids, peptides, polypeptides, proteins, lipids, carbohydrates, glycoaminoglycans, nucleic acids and combinations thereof. The desired agents can be naturally occurring or synthetic in nature, and can include polymers, beads, nano and microparticles, and amphiphilic molecules. In some embodiments, the agent is modified to comprise a photoactivatable group. As above, suitable agents comprising a photoactivatable group preferably are organic molecules including, but not limited to, amino acids, peptides, polypeptides, proteins, lipids, carbohydrates, glycoaminoglycans, nucleic acids and combinations thereof. In these embodiments, the agent comprising the photoactivatable group may be applied to the target membrane followed by photoactivation to provide a mucous membrane modified with the agent comprising a photoactivatable group.

In some embodiments, the agent non-covalently binds to one or components of the mucous membrane, e.g., lipids, carbohydrates, glycosaminoglycans or protein contained with the mucous membrane. Suitable binding agents include, but are not limited to, antigen binding proteins, lectins, dendrimers, aptamers, and nucleic acids. Other binding agents may include catechols. In some embodiments, the binding agents may comprise a functional group to enable further modification. Suitable functional groups may be provided as described above via homobifunctional linkers, heterobifunctional linkers, photoactivatable linkers, and click chemistry functionalities.

In some embodiments, the agents described above may comprise a first binding partner moiety that is specifically recognized or bound by a second binding partner moiety. In some embodiments, the first binding partner moiety is a hapten, nucleic acid, polypeptide or carbohydrate and the second binding partner moiety an antigen binding protein specific for the hapten, a nucleic acid that is complementary to a nucleic acid used as the first binding partner moiety, an antigen binding protein or protein that specifically binds to a polypeptide that is the first binding partner moiety (for example avidin and biotin), or an antigen binding protein or lectin that binds to a carbohydrate that is the first binding partner moiety. In other embodiments of the invention the first and second binding partners are synthetic in nature and might comprise synthetic supramolecular complexes.

In some embodiments, the agent is a sensitizing agent. Suitable sensitizing agents include, but are not limited to, redox-active agents, light sensitive agents, agents that are transformed upon irradiation, agents that promote the association of a second agent with the mucous membrane, thus increasing the effectiveness of the second agent. Examples of redox-active agents include but are not limited to reducing agents and oxidizing agents. For example, pretreatment of a mucous membrane system with dithiothreitol can lead to the generation of free thiol groups in the mucous membrane system, thus leading to sensitive reactions of maleimide-containing agents with the mucous membrane system. Alternative, a sensitizing agent may give rise to the generation of reactive radical species upon illumination, which in turn sensitizes the mucous membrane system to reaction with additional agents. Similar, a sensitizing agent might lead to a preferred pH in a mucous membrane system to sensitize the system to an interaction with an added or already present agent. A sensitizing react might also interact or decrease the concentration of an inhibitor of a reaction or physical interaction, thus the presence of the sensitizer will in turn promote the otherwise inhibited transformation in the mucous membrane.

In some embodiments, one or more additional agents (i.e., second, third, fourth, or fifth agents, etc.) are applied to the target mucous membrane either with the first agent or after the first agent has been applied. In preferred embodiments, the second agent promotes, enhances, or potentiates the holding of the aqueous component of the mucous membrane in place. In some preferred embodiments, the part of the mucous membrane is a tear film and the agent promotes holding the aqueous component of the tear film in place such that tear break-up time is increased. A variety agents may be utilized in this context, including, but not limited to, mucins, synthetic mucins, mucin analogs, proteins, peptides, dendrimers, nano- and microscale particles, hydrogels, polyelectrolytes, polyelectrolyte multilayers, hydrophilic polymers, amphiphiles, macromolecules, cross-linked hydrophilic polymers, deliquescent molecules, nanoporous substances, rheological modifiers, agents that influence the disjoining pressure of thin liquid films, nanostructured hydrogels, polymeric scaffolds, a mesh or patch that contains micro-scale or nano-scale topography, hyaluronic acid, polymeric brushes, cross-linked collagen, photoactivatable crosslinkers, riboflavin cross-linkers, modified celluloses, hydroxypropylcellulose, hydroxymethylcellulose, dextrans, glycerin, metal salts, polyethyleneglycol, liquid crystals, agents that modify the topography of the mucous membrane system to influence contact line motion, and combinations thereof. The present invention includes also the use of superabsorbent polymers, such as those prepared from sodium polyacrylate, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile and those that are found in diapers.

The present invention is not limited to the use of any particular mucin or mucin-like molecules. The mucins may be synthetic or derived from natural sources. Suitable natural sources include mammalian mucins, especially human mucins, as well as non-vertebrate mucins. Synthetic mucins, mucin fragment or mucin analogs may be made by cloning suitable mucin genes (e.g., human mucin genes) and expressing the cloned mucin via a vector in a suitable host cell (prokaryotic or eukaryotic).

In some embodiments of the invention, the agents added to the mucous membrane system change the rheological properties of the mucous membrane system to influence the tear break-up time. Examples of rheological modifiers include modified hydroxycellulose, block copolymers, suspensions of particles and polymers, amphiphilic assemblies, mixtures of two polymers or mixtures of polymers and amphiphiles and materials that form physical gels. The mixtures may be designed such that gelation or modification of rheological properties occurs on dilution in the aqueous component of the tear film. This includes designs of mixtures such that dilution leads to an increase in viscous and/or elastic rheological properties of the mucous membrane system. These embodiments of the invention include modifiers that lead to viscoelastic phases in the mucous membrane system, including Bingham plastic fluids, psueodoplastic fluids, and rheopectic fluids, and fluids that thin or thicken in viscosity when sheared. In some embodiments of the invention, the agents change the rheology of the lipid layer of the mucous membrane system in other embodiments they change the rheological properties of other layers in the mucous membrane system.

In other embodiments of the invention, the agents added to the system interact physically or reactively to change the disjoining pressure of thin films of liquids within the mucous membrane system. The disjoining pressure can change to influence the tear break-up time. Examples of agents that are not limiting but illustrate agents that can change disjoining pressures of thin films includes micro and nanoparticles, polymers, amphiphiles and other supramolecular assemblies. It is also possible to influence disjoining pressures in mucous membrane systems by adding ionic species to the system that modify the charges of interfaces of thin films of liquids in mucous membrane systems. The scope of the invention covers changes to the disjoining pressure in the aqueous or lipid films of the mucous membrane system. In other embodiments of the invention, the agents added to the system interact physically or reactively to change the equilibrium or dynamic contact angle and wetting of the lipid or aqueous components of the mucous membrane.

A wide variety of nano- and micro-scale particles may be utilized in the present invention. In some embodiments, nanometer to submicrometer sized biocompatible particles, such as spherical (e.g., beads) and/or non-spherical (e.g., oblongs, needles, cubes, tetrahedral, mushroom-like structures, haybale-like structures) particles or electrospun polymers, are applied (e.g., either directly or indirectly) to the mucous membrane. For example, application of biocompatible particles to a mucous membrane results in the creation of knobs, ridges, spikes, undulations, and the like on the mucous membrane. Microbeads have a size generally ranging from about 1 to about 500 micrometers, submicron beads generally are considered to range from 100 nm to 1,000 nm while nanobeads have a size generally ranging from about 1 to about 100 nanometers. Microbeads may further comprise micro- (i.e., from 1 to 100 micrometers) or nano-scale (0.1 to 1000 nanometer) features on the surface of the bead. Nanobeads and submicron beads may further comprise nanoscale features (i.e., 0.1 to 500 nanometer features) on the surface of the bead. In some embodiments, the agent is presented in the form of a bead or particle, such as silver nanoparticles.

In some embodiments, the biocompatible particles are biodegradable. In some embodiments, the biocompatible particles are not biodegradable. The biocompatible particles, for example, are modified with surface chemistry cross-linkers that allow attachment and immobilization of desired active agents, extracellular matrix compounds, polyelectrolytes, etc. as described further herein. It is contemplated that the incorporation of modified biocompatible particles, for example, facilitates wetting of the mucous membrane and improves hydration. In some embodiments, the biocompatible particles are functionalized with mesoscopic cross-linkers to, for example, broadly enable covalent chemistry in the mucous membrane. In some embodiments, cross-linkers are attached to negatively charged biocompatible particles. In some embodiments, the biocompatible particles comprise layers of multiple different constituents for altering the mucous membrane, or a single constituent for producing a desired characteristic in a target mucous membrane. For example, spherical particles such as beads placed on a mucous membrane comprise, or upon which are layered, one or more intermixed species of polyelectrolytes, mucins, proteins with hydrolysable bonds, proteins with enzymatically cleavable bonds, and the like as previously described. In some embodiments, antimicrobials, either alone or in combination with other compositions, are also applied to the biocompatible particles. Antimicrobials include, but are not limited to, antibiotics, metal based antimicrobial compositions comprising silver (e.g., ionic silver, elemental silver, silver nanoparticles), copper, chlorhexadine, iodine, selenium, triclosan-based antimicrobials, thiabendazole-based antimicrobials, isothiazolinone-based antimicrobials, zinc-pyrithione-based antimicrobials, and/or 10'-oxybisphenoxarsine-based antimicrobials (OBPA). The present invention is not limited by the type of antimicrobial used.

In some embodiments, the size of the biocompatible particles, such as beads, are at least 1 nm, at least 5 nm, at least 10 nm, at least 20 nm, at least 50 nm, at least 100 nm, at least 200 nm, at least 300 nm, at least 500 nm, or at least 800 nm in diameter. In some embodiments a mixture of dimensions of topographically altering beads, threads or other non-spherical structures are used. In some embodiments, beads and other spherical and non-spherical particles or threads contain their own surface topography. For example, the bead surface may comprise undulations, indentations, tunnels, holes, knobs, ridges, etc. Some bead surfaces may possess random or deterministic chemical patches. Some particles are designed to undergo self-assembly in the mucous membrane system. Some particles are solid and some are hollow. Spherical particles, such as beads, may or may not be inert and may, for example, be magnetic. Magnetic beads comprise, for example, a magnetic core or magnetic particles. Examples of different bead compositions are found at, for example, U.S. Pat. Nos. 5,268,178, 6,458,858, 6,869,858, and 5,834,121, each of which is incorporated herein by reference in its entirety.

As described above, in some embodiments, biocompatible particles of the present invention used for treatment of mucous membranes are coated with layers of polyelectrolytes, mucins, mucin fragments, mucin analogs, synthetic mucins, antimicrobials, proteins with hydrolysable bonds, amphiphiles, surfactants and proteins with enzymatically cleavable bonds, etc. and other compositions wherein the surface compliance of the beads is maintained for optimal mucous membrane characteristics. For example, the compliance conferred on the biocompatible particles are contemplated to be of optimal stiffness (e.g., not too soft, not too hard) such that dewetting or increased tear breakup time are effected. In some embodiments, the biocompatible particles are layered with polyelectrolytes, mucins, antimicrobials, etc. wherein substrate stiffness of at least 100 Pa, 250 Pa, 500 Pa, 1 kPa, at least 5 kPa, at least 8 kPa, at least 10 kPa, at least 20 kPa, at least 40 kPa, at least 60 kPa, at least 80 kPA is realized as measured using the methods of Engler et al. (2004). In preferred embodiments, substrate compliance of the compositions as applied to biocompatible particles is at least 400 Pa, 1 kPa to about 80 kPa or 100 kPa. It will be recognized that hardness within these limit are contemplated without specifically listing all such hardnesses, for example, 10, 20, 30, 40, 50, 60, or 70 kPa limits as upper or lower ranges are all contemplated by the present invention.

In some embodiments, compositions applied to the biocompatible particles (e.g., beads, needles, etc.) are time released, such that the compositions that are applied to the biocompatible particle is released over a period of time, for example 3 hours, 5 hours, 10 hours, 1 day, several days, one week, several weeks, etc. thereby providing short and/or long term treatment of the mucous membrane. In some embodiments, compositions are released in differing temporal timelines such that one composition is released first followed by release of a second composition. It is noted that there can be overlap in release of multiple compositions. The overlap can be complete (i.e. two or more compositions released at same time for same interval) or release kinetics of multiple compositions can be complex in timing with differential overlapping patterns.

In some embodiments, one or more polymers or polymer layers are applied to the target mucous membrane. In some embodiments, polymer is in the form of polymer multilayer. In some embodiments, the multilayer structures comprise layers of polymers that form polyelectrolytes, while in other embodiments, the multilayers comprise polymers that do not have a charge (i.e., non-ionic polymers) or a combination of charged and uncharged polymer layers. In some embodiments, it is contemplated that polyelectrolyte films built-up by the alternated adsorption of cationic and anionic polyelectrolyte layers constitute a novel and promising technique to modify mucous membranes in a controlled way. One of the most important properties of such multilayers is that they exhibit an excess of alternatively positive and negative charges (Caruso et al., 1999, J Am Chem Soc 121:6039; Ladam et al., 2000, Langmuir 16:1249). Not only can this constitute the motor of their buildup (Joanny, 1999, Eur. Phys. J. Biol. 9:117), but it allows, by simple contact, to adsorb a great variety of compounds such as dyes, particles (Cassagneau et al., 1998, J. Am. Chem. Soc. 120:7848; Caruso et al., 1999, Langmuir 15:8276; Lvov et al., 1997, Langmuir 13:6195), clay microplates (Ariga et al., 1999, Appl. Clay Sci. 15:137) and proteins (Keller et al., 1994, J. Am. Chem. Soc. 116:8817; Lvov et al., 1995, J. Am. Chem. Soc. 117:6117; Caruso et al., 1997, Langmuir 13:3427).

In some embodiments, the polymer multilayers, such as polyelectrolyte multilayers, are nanoscale in dimension. Accordingly, in some embodiments, the polymer multilayers are from about 1 nm to 1000 nm thick, from about 1 nm to 500 nm thick, from about 1 nm to 100 nm thick, from about 1 nm to about 25 nm thick, from about 1 nm to about 10 nm thick, or less than about 500 nm, 100 nm, 25 nm or 10 nm thick. In some embodiments, the polymer multilayers exhibit a compliance, measured in kilopascals (kPa) of from about 3 to about 500 kPa, about 7 to about 250 kPa, about 10 to about 250 kPa or from about 10 to about 200 kPa.

Polyelectrolyte layers are formed by alternating applications of anionic polyelectrolytes and cationic polyelectrolytes to surfaces to form a polyelectrolyte layer. The layers can be used to deliver an active agent to a mucous membrane. Preferably, at least four layers, and, more preferably, at least six layers are used to form the polyelectrolyte multilayer.

In some embodiments, the cationic polyelectrolyte used is PLL and the anionic polyelectrolyte used is poly(L-glutamic acid) (PGA). Indeed, the use of a variety of polyelectrolytes is contemplated, including, but not limited to, poly(ethylene imine) (PEI), poly(allylamine hydrochloride) (PAH), poly (sodium 4-styrenesulfonate) (PSS), poly(acrylic acid) (PAC), poly(maleic acid-co-propylene) (PMA-P), poly (acrylic acid) (PAA), and poly(vinyl sulfate) (PVS). It is also possible to use naturally occurring polyelectrolytes, including hyaluronic acid and chondroitin sulfate.

In still further embodiments, the polymer is a dendrimer, grafted polymer, or star architecture polymer. In other embodiments, the multilayer responds to or is organized in the presence of an electric field, for example an electric field formed by placing electrodes on either side of a target mucous membrane.

Other suitable methods for preparing polyelectrolyte multilayers include those described, for example, in Cho and Char, Langmuir 20:4011-4016, 2004; Okamura et al., Adv. Mater. 21, 4388-92 (2009), Cho et al., Adv. Mat. 13(14): 1076-1078 (2001); and U.S. pat. Publ. 2010/0062258; the entire contents of each of which is incorporated herein by reference. Suitable methods include layer by layer deposition, formation on SAMs, and spin coating assisted assembly.

In other embodiments, the polyelectrolyte multilayer is prefabricated outside the mucous membrane system, and transferred into it post-fabrication. The prefabricated multilayer system can be spatially patterned to introduce a topography into the mucous membrane system to influence the stability of the tear film. It can also introduce a chemical pattern to influence the stability of the tear film. The multilayer system may also slowly release an agent that impacts the stability of the tear film. In a preferred embodiment, the polyelectrolyte multilayer is transferred into the mucous membrane system using a water-soluble backing such as polyvinylalcohol. In other embodiments, the polymer multilayer is transferred into the mucous membrane system using a contact lens.

Cationic polymers useful in the present invention can be any biocompatible water-soluble polycationic polymer, for example, any polymer having protonated heterocycles attached as pendant groups. As used herein, "water soluble" means that the entire polymer must be soluble in aqueous solutions, such as buffered saline or buffered saline with small amounts of added organic solvents as co-solvents, at a temperature between 20 and 37° Centigrade. In some embodiments, the material will not be sufficiently soluble (defined herein as soluble to the extent of at least one gram per liter) in aqueous solutions per se but can be brought into solution by grafting the polycationic polymer with water-soluble polynonionic materials such as polyethylene glycol.

Representative cationic polymers include natural and unnatural polyamino acids having net positive charge at neutral pH, positively charged polysaccharides, and positively charged synthetic polymers. Examples of suitable polycationic materials include polyamines having amine groups on either the polymer backbone or the polymer side chains, such as poly-L-lysine (PLL) and other positively charged polyamino acids of natural or synthetic amino acids or mixtures of amino acids, including, but not limited to, poly(D-lysine), poly(ornithine), poly(arginine), and poly (histidine), and nonpeptide polyamines such as poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly (N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan. In some embodiments, PLL is a preferred material.

In general, the polymers must include at least five charges, and the molecular weight of the polycationic material must be sufficient to yield the desired degree of binding to a tissue or other surface, having a molecular weight of at least 1000 g/mole.

Polyanionic materials useful in the present invention can be any biocompatible water-soluble polyanionic polymer, for example, any polymer having carboxylic acid groups attached as pendant groups. Suitable materials include alginate, carrageenan, furcellaran, pectin, xanthan, hyaluronic acid, heparin, heparin sulfate, chondroitin sulfate, dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone. Polyamino acids of predominantly negative charge are also suitable. Examples of these materials include polyaspartic acid, polyglutamic acid, and copolymers thereof with other natural and unnatural amino acids. Polyphenolic materials such as tannins and lignins can be used if they are sufficiently biocompatible. Preferred materials include alginate, pectin, carboxymethyl cellulose, heparin and hyaluronic acid.

In some embodiments, the multilayer structures are formed from uncharged polymers or from a combination of charged and uncharged polymers. Examples of uncharged polymers include, but are not limited to, dextran, dextran sulfate, diethylaminoethyl (DEAE)-dextran, hydroxyethyl cellulose, ethyl(hydroxyethyl) cellulose, acrylamide, polyethylene oxide, polypropylene oxide, polyethylene oxide-polypropylene oxide copolymers, PAAN$_a$, Ficoll, polyvinylpyrolidine, and polyacrylic acid.

In some embodiments, the multilayer structures are formed from one or more amphoteric polymers, alone in combination with the other polymers described herein. In some embodiments, the amphoteric polymers comprise one or more of acrylic acid (AA), DMAEMA (dimethylaminoethyl methacrylate), APA (2-aminopropyl acrylate), MorphEMA (morpholinoethyl methacrylate), DEAEMA (diethylaminoethyl methacrylate), t-ButylAEMA (t-butylaminoethyl methacrylate), PipEMA (piperidinoethyl methacrylate), AEMA (aminoethyl methacrylate), HEMA (2-hydroxyethyl methacrylate), MA (methyl acrylate), MAA (methacrylic acid) APMA (2-aminopropyl methacrylate), AEA (aminoethyl acrylate). In some embodiments, the amphoteric polymer comprises (a) carboxylic acid, (b) primary amine, and (c) secondary and/or tertiary amine. The amphoteric polymers have an isoelectric point of 4 to 8, preferably 5 to 7 and have a number average molecular weight in the range of 10,000 to 150,000.

The polymers can be applied to the mucous membrane system by a variety of methods. In some embodiments, it is contemplated that the polymer or polymer multilayer, is applied, preferably sequentially, to the mucous membrane using either a pump (including syringes, ink jet printers, and electrojets) or aerosol spray. In some embodiments, the polymer is delivered with a second agent, and that upon dilution of the second agent in the tear film, the polymer is deposited into the mucous membrane system to improve the performance of the mucous membrane system such as but not limited to an increase in the tear-film break-up time, a decrease in fluoresecin staining, a decrease in lisamine green staining, a decrease in Rose Bengal staining, a decrease in redness, a decrease in ocular discharge, and an increase in patient comfort with diminishing clinical symptoms (itchy, burning, foreign body sensation, sandy, gritty sensations). An exemplary second agent would be an amphiphilic substance or an ionic substance. An exemplary polymer would be a polyelectrolyte or a hydrophobically modified polymer. In other embodiments, particle bombardment is utilized. In other embodiments, the use of a brush including an air brush is contemplated. In other embodiments, a sponge is utilized. In other embodiments a solid support or stamp such as an elastomeric material, for example, PDMS (polydimethylsiloxane), silicone, hydrogel or latex, is used to support the polymer or polymer multilayer and mechanically transfer the agent onto the target mucous membrane. In these embodiments, the polymer multilayers are pre-formed on the stamp. In further embodiments, nano- or micro-particles are arranged on the stamp for delivery to the mucous membrane. In other embodiments eye drops are used or a contact lens is used. In other embodiments a sheet of a water soluble polymer is used.

In some embodiments, the polymers are applied to a target mucous membrane by a spray, such as via a pump, nebulizing or aerosol device. In some embodiments, the polymer layers are applied sequentially. In embodiments where the agents are supplied as aerosols, a propellant is used to provide the force for expulsion from the container. In general, for aerosol delivery, the ingredients of the composition are mixed to form a substantially homogenous solution, slurry, dispersion, or the like. For two-part systems, each part is mixed. The compositions are placed in an appropriate container and the propellant is added using conventional techniques, such as cold filling or pressure filling techniques. The composition can be delivered using a commercially available aerosol sprayer such as, for example, the Prevail™ aerosol spray unit available from Precision Valve Corporation, NY, USA, which has a modular power unit and refillable container jar. The propellant is a mixture of propane, isobutane, and dimethyl ether.

The compositions can also be delivered using a syringe outfitted with a spray head, or a dual spray device outfitted with a spray head and, optionally, a mixing chamber. The device may include a meter so that the quantity of applied composition can be controlled sprays can also be delivered using standard squeeze bottles found in many commercially available nasal sprays.

Any of a number of propellants known to those skilled in the art can be used, provided that it is chemically inert to the other ingredients of the composition and safe for use with mucous membranes. Suitable propellants include vinyl chloride and mixtures of vinyl chloride and dichlorodifluoromethane, other fluorochlorohydrocarbons known as the Freons and the Genetrons, and blends of fluorochlorohydrocarbons, chlorinated hydrocarbons, and hydrocarbons. Examples of fluorochlorohydrocarbons include trichloromonofluoromethane, dichlorodifluoromethane, dichloromonofluoromethane, 2-tetrafluoroethane, 1,1-dichloro-1,2,2-tetraf-luoroethane, 1-chloro-1,1-difluoroethane, 1,1-difluoroethane, and octofluorocyclobutane, and mixtures thereof. Examples of hydrocarbons include liquefied petroleum gases like propane, isobutane, and N-butane and mixtures thereof. Dimethyl ether is another propellant. Compressed gas propellants that are preferably non-toxic, non-flammable, and inert can be used. Examples include carbon dioxide, nitrous oxide and N2 and the like. Mixtures of the above are often used.

In some embodiments, the agents described above are applied to the mucous membrane by microfluidics printing, microstamping (U.S. Pat. Nos. 5,512,131 and 5,731,152, both of which are incorporated by reference herein in their entirety), or microcontact printing (PCT Publication WO 96/29629, incorporated by reference herein in its entirety). In other embodiments, the agents are applied to the mucous membrane via a pulse jet such as an inkjet printer. Examples of suitable inkjet printers for application of biological fluids include those described in U.S. Pat. No. 7,128,398, WO 95/25116 and WO 98/41531, each of which is incorporated by reference in its entirety. In other embodiments, the agents are applied by a drop dispensers such as the tip of a pin or in an open capillary and, touch the pin or capillary to the surface of the substrate. Such a procedure is described in U.S. Pat. No. 5,807,522. When the fluid touches the surface, some of the fluid is transferred. In other embodiments, the agents are applied be pipetting, micro-pipetting or positive displacement pumps such as the Biodot equipment (available from Bio-Dot Inc., Irvine Calif., USA).

In preferred embodiments the agents are applied by simple topical application as an ointment, cream, gel or drop. The drop/ointment/cream/gel can have a variety of viscosities. In some embodiments the drops are applied sequentially in other embodiments a single application is employed. In preferred embodiments the chemistry and/or biophysical attributes of the cellular surface of the mucous membrane are altered in such a way as to optimize the effectiveness of a second drop being applied that interacts with the engineered (modified) mucous membrane surface to bring about desirable effects to a users benefit. Such desirable properties are exemplified by but not limited to increased stability of the tear film, (i.e., increased resistance to film breakup, decreased rate of expansion of dewetting lines upon film breakup), improved lubrication properties, increased wetting of cells, improved adhesion/stability of native mucous membrane films, decreased mucous accumulation, improved flushing of fluids across the mucous membrane and similar properties.

A variety of additional agents may be applied to the mucous membrane in conjunction with the agents described above. In some embodiments, the active agents are drug agents, for example, anti-inflammatory drugs, anti-microbial drugs, anti-fungal drugs, vitamins, and/or analgesics. The active agents may be associated with (e.g., delivered to) the target mucous membrane via covalent binding interactions or non-covalent binding interaction as described above and may be incorporated into polymers or polymer multilayers.

Accordingly, in some embodiments, the present invention provides the delivery of trophic factors, including, but not limited to, agrin, amphiregulin, artemin, cardiotrophin-1, epidermal growth factors including EGF; fibroblast growth factors (e.g., FGF-1, FGF-2, FGF-3, FGF-4, FGF-5, FGF-6, and FGF-7); LIF, CSF-1, CSF-2, CSF-3, erythropoietin, endothelial cell growth factors including ECGF; FGF- and ECGF-related growth factors (e.g., endothelial cell stimulating angiogenesis factor, tumor angiogenesis factor, retina-derived growth factor (RDGF), vascular endothelium growth factor (VEGF), brain-derived growth factors (BDGF-A and B), astroglial growth factors (AGF 1 and 2), omentum-derived growth factor, fibroblast-stimulating factor (FSF), and embryonal carcinoma-derived growth factor (ECDGF)); neurotrophic growth factors (e.g., nerve growth factors (NGFs), neurturin, brain-derived neurotrophic factor (BDNF), neurotrophin-3, neurotrophin-4, and ciliary neurotrophic factor (CNTF)); glial growth factors (e.g., GGF-I, GGF-II, GGF-III, glia maturation factor (GMF), and glial-derived neurotrophic factor (GDNF)); liver growth factors (e.g., hepatopoietin A, hepatopoietin B, and hepatocyte growth factors including HGF); prostate growth factors including prostate-derived growth factors (PGFs); mammary growth factors including mammary-derived growth factor 1 (MDGF-1) and mammary tumor-derived factor (MTGF); heart growth factors including nonmyocyte-derived growth factor (NMDGF); melanocyte growth factors including melanocyte-stimulating hormone (MSH) and melanoma growth-stimulating activity (MGSA); angiogenic factors (e.g., angiogenin, angiotropin, platelet-derived ECGF, VEGF, and pleiotrophin); transforming growth factors including TGF-α and TGF-β; TGF-like growth factors (e.g., TGF-beta$_1$, TGF-beta$_2$, TGF-beta$_3$, GDF-1, CDGF, tumor-derived TGF-like factors, ND-TGF, and human epithelial transforming factor); regulatory peptides with growth factor-like properties (e.g., bombesin and bombesin-like peptides ranatensin and litorin, angiotensin, endothelin, atrial natriuretic factor, vasoactive intestinal peptide, and bradykinin); platelet-derived growth factors including PDGF-A, PDGF-B, and PDGF-AB; neuropeptides (e.g., substance P, calcitonin gene-regulated peptide (CGRP), and neuropeptide Y); neurotransmitters and their analogs including norepinephrine, acetylcholine and carbachol; hedgehog, heregulin/neuregulin, IL-1, osteoclast-activating factor (OAF), lymphocyte-activating factor (LAF), hepatocyte-stimulating factor (HSF), B-cell-activating factor (BAF), tumor inhibitory factor 2 (TIF-2), keratinocyte-derived T-cell growth factor (KD-TCGF), IL-2, IL-3, IL-4, IL-5, IL-6, IL-7, IL-8, IL-9, IL-10, IL-11, stromal cell-derived cytokine (SCDC), IL-12, IL-13, IL-14, IL-15, insulin, insulin-like growth factors including IGF-1, IGF-2, and IGF-BP; interferons including INF-alpha, INF-beta, and INF-gamma; leptin, midkine, tumor necrosis factors (TNF-alpha and beta), netrins, saposins, semaphorins, somatrem, somatropin, stem cell factor, VVGF, bone morphogenetic proteins (BMPs), adhesion molecules, other cytokines, heparin-binding growth factors, and tyrosine kinase receptor ligands. In some embodiments, the agent is a peptide such as AcEEED (SEQ ID NO:1), which is the N terminal peptide for alpha smooth muscle actin and has been shown to inhibit contractile properties of myofibroblasts.

In some embodiments, the present invention provides the delivery of ECM components, including, but not limited to native constructs, fragments of native constructs and synthetic analogs of: extracellular matrix proteins, matricellular proteins, hyaluronic acids, chodroitin sulfates, reconstituted basement membrane-like complexes derived from eukaryotic cell lines, collagens, fibronectin, laminin, VCAM-1, vitronectin and gelatin, a bacterial extracellular matrix, a gel matrix, and polymeric matrices. In some embodiments, the active agents are integrin binding sequences exemplified by, but not limited to RGD, EILDV, VCAM-1 and their recombined or synthetic analogs, enzymes, enzyme inhibitors, and polypeptides.

In some embodiments, the present invention provides the delivery of enzymes, including, but not limited to, exopeptidases and endopeptidases (also known as proteases and proteinases), including but not limited to the serine proteinases chymotrypsin, trypsin, elastase, and kallikrein, bacterial enzymes, the cysteine proteases papain, actinin, bromelain, cathepsins, cytosolic calpains, parasitic proteases, aspartic proteinases, the pepsin family of proteases pepsin and chymosin, lysosomal cathepsins D, renin, fungal proteases, the viral proteases, AIDS virus retropepsin, and the metalloproteinases (MMPs), collagenases, Maggott enzyme, MMP1, MMP2, MMP8, MMP13, gelatinases, MMP2, MMP9, MMP3, MMP7, MMP10, MMP11, and MMP12.

In some embodiments, the present invention provides the delivery of enzyme inhibitors, including, but not limited to captopril, thiorphan, phosphoramidon, teprotide, protease and proteinase inhibitors, metalloproteinase inhibitors and exopeptidase inhibitors.

In some embodiments, the present invention provides the delivery of antimicrobial peptides. Exemplified by but not limited to defensins, including, but not limited to, alpha-defensins HNP 1, 2, 3 and 4, and beta-defensins HBD-1 and HBD-2. A host of other defense peptides could be integrated with use of the invention. including magainins, cathelicidins, and the like. A non limiting list can be found at the antimicrobial peptide updated data base ((APD, /aps.unmc.edu/AP/main.php).

In some embodiments, the present invention provides the delivery of polypeptides, including, but not limited to, fibronectin, serotonin, PAF, PDEGF, TNFa, IL1, IL6, IGF, IGF-1, IGF-2, IL-1, PDGF, FGF, KGF, VEGF, bradykinin, prothymosin-alpha, and thymosin-alpha1.

In some embodiments, the present invention provides the delivery of antimicrobials, including, but not limited to, magainin (e.g., magainin I, magainin II, xenopsin, xenopsin precursor fragment, caerulein precursor fragment), magainin I and II analogs (e.g., PGLa, magainin A, magainin G, pexiganin, Z-12, pexigainin acetate, D35, MSI-78A, MGO (K10E, K11E, F12W-magainin 2), MG2+(K10E, F12W-magainin-2), MG4+(F12W-magainin 2), MG6+ (f12W, E19Q-magainin 2 amide), MSI-238, reversed magainin II analogs (e.g., 53D, 87-ISM, and A87-ISM), Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME (1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 ((+/−) 1-(4-aminobutyl)-6-benzylindane), PM2c ((+/−)-6-benzyl-1-(3-carboxypropyl)indane), PM3 ((+/−)1-benzyl-6-(4-aminobutyl)indane), tachyplesin, buforin I or II, misgurin, melittin, PR-39, PR-26, 9-phenylnonylamine, (KLAKKLA)n(SEQ ID NO:2), (KLAKLAK)n(SEQ ID NO:3), where n=1, 2, or 3, (KALKALK)3(SEQ ID NO:4), KLGKKLG)n (SEQ ID NO:5), and (KAAKKAA)n(SEQ ID NO:6), wherein n=1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG1, 1bAMP, snakin, lipid transfer proteins, and plant defensins.

In some embodiments, the present invention provides the delivery of antimicrobials, including, but not limited to, loracarbef, cephalexin, cefadroxil, cefixime, ceftibuten, cefprozil, cefpodoxime, cephradine, cefuroxime, cefaclor, neomycin/polymyxin/bacitracin, dicloxacillin, nitrofurantoin, nitrofurantoin macrocrystal, nitrofurantoin/nitrofuran mac, dirithromycin, gemifloxacin, ampicillin, gatifloxacin, penicillin V potassium, ciprofloxacin, enoxacin, amoxicillin, amoxicillin/clavulanate potassium, clarithromycin, levofloxacin, moxifloxacin, azithromycin, sparfloxacin, cefdinir, ofloxacin, trovafloxacin, lomefloxacin, methenamine, erythromycin, norfloxacin, clindamycin/benzoyl peroxide, quinupristin/dalfopristin, doxycycline, amikacin sulfate, vancomycin, kanamycin, netilmicin, streptomycin, tobramycin sulfate, gentamicin sulfate, tetracyclines, framycetin, minocycline, nalidixic acid, demeclocycline, trimethoprim, miconazole, colistimethate, piperacillin sodium/tazobactam sodium, paromomycin, colistin/neomycin/hydrocortisone, amebicides, sulfisoxazole, pentamidine, sulfadiazine, clindamycin phosphate, metronidazole, oxacillin sodium, nafcillin sodium, vancomycin hydrochloride, clindamycin, cefotaxime sodium, co-trimoxazole, ticarcillin disodium, piperacillin sodium, ticarcillin disodium/clavulanate potassium, neomycin, daptomycin, cefazolin sodium, cefoxitin sodium, ceftizoxime sodium, penicillin G potassium and sodium, ceftriaxone sodium, ceftazidime, imipenem/cilastatin sodium, aztreonam, cinoxacin, erythromycin/sulfisoxazole, cefotetan disodium, ampicillin sodium/sulbactam sodium, cefoperazone sodium, cefamandole nafate, gentamicin, sulfisoxazole/phenazopyridine, tobramycin, lincomycin, neomycin/polymyxin B/gramicidin, clindamycin hydrochloride, lansoprazole/clarithromycin/amoxicillin, alatrofloxacin, linezolid, bismuth subsalicylate/metronidazole/tetracycline, erythromycin/benzoyl peroxide, mupirocin, fosfomycin, pentamidine isethionate, imipenem/cilastatin, troleandomycin, gatifloxacin, chloramphenicol, cycloserine, neomycin/polymyxin B/hydrocortisone, ertapenem, meropenem, cephalosporins, fluconazole, cefepime, sulfamethoxazole, sulfamethoxazole/trimethoprim, neomycin/polymyxin B, penicillins, rifampin/isoniazid, erythromycin estolate, erythromycin ethylsuccinate, erythromycin stearate, ampicillin trihydrate, ampicillin/probenecid, sulfasalazine, sulfanilamide, sodium sulfacetamide, dapsone, doxycycline hyclate, trimenthoprim/sulfa, methenamine mandelate, plasmodicides, pyrimethamine, hydroxychloroquine, chloroquine phosphate, trichomonocides, anthelmintics, atovaquone, bacitracin, bacitracin/polymyxin b, gentamycin, neomycin/polymyxin/dexameth, neomycin sulf/dexameth, sulfacetamide/prednisolone, sulfacetamide/phenylephrine, tobramycin sulfate/dexameth, bismuth tribromophenate, silver ion compounds, silver nanoparticles, zerovalent silver, multivalent silver, elemental silver, and silver containing compounds such as silver sulfadiazine and related compounds.

In some embodiments, the present invention provides the delivery of antivirals, including, but not limited to, amantadine, acyclovir, foscarnet, indinavir, ribavirin, enfuvirtide, emtricitabine, lamivudine, abacavir sulfate, fomivirsen, valacyclovir, tenofovir, cidofovir, atazanavir, amprenavir, delavirdine mesylate, famciclovir, adefovir, didanosine, efavirenz, trifluridine, inidinavir, lamivudine, vidarabine, lopinavir/ritonavir, ganciclovir, zanamivir, abacavir/lamivudine/zidovudine, lamivudine/zidovudine, nelfinavir, nelfinavir mesylate, nevirapine, ritonavir, saquinavir, saquinavir mesylate, rimantadine, stavudine, docosanol, zalcitabine, idoxuridine, zidovudine, zidovudine/didanosine, valganciclovir, penciclovir, lamivudine, and oseltamivir.

In some embodiments, the present invention provides the delivery of antifungals, including, but not limited to, amphotericin B, nystatin, nystatin/triamcinolone, itraconazole, ketoconazole, miconazole, sulconazole, clotrimazole, clotrimazole/betamethasone, enilconazole, econazole, oxiconazole, tioconazole, terconazole, butoconazole, thiabendazole, flucytosine, butenafine, ciclopirox, haloprogin, naftifine, tolnaftate, natamycin, undecylenic acid, mafenide, dapsone, clioquinol, clioquinol/hydrocortisone, potassium iodide, silver sulfadiazine, gentian violet, carbol-fuchsin, cilofungin, sertaconazole, voriconazole, fluconazole, terbinafine, caspofungin, other topical azole drugs, and griseofulvin.

In some embodiments, the present invention provides the use and delivery of buffering agents, including, but not limited to, Maleic acid, Phosphoric acid, Glycine, Chloroacetic acid, Formic acid, Benzoic acid, Acetic acid, Pyridine, Piperazine, MES, Bis-tris, Carbonate, ACES, ADA MOPSO, PIPES, Phosphoric acid, BES, MOPS, TES, HEPES, DIPSO, TAPSO, Triethanolamine, HEPSO, Tris, Tricine, Bicine, TAPS, Borate, Ammonia, CHES, Ethanolamine, CAPSO, Glycine, Carbonate, CAPS, Methylamine, Piperidine, and Phosphoric acid.

In some embodiments, the present invention provides the delivery of vitamins and minerals, including, but not limited to, Vitamin A, Carotenoids, Vitamin D, Vitamin E, Vitamin K, Vitamin C/ascorbic acid, B1/thiamin, B2/riboflavin, B3/niacin, B5/pantothenic acid, B6/pyridoxine, B12/cobalamin, Biotin, Calcium, Magnesium, Phosphorus, Sodium, Chloride, Potassium, Boron, Chromium, Copper, Iodine, Iron, Manganese, Selenium, and Zinc.

In some embodiments, the present invention provides the delivery of analgesics, including, but not limited to, acetaminophen, anileridine, acetylsalicylic acid, buprenorphine, butorphanol, fentanyl, fentanyl citrate, codeine, rofecoxib, hydrocodone, hydromorphone, hydromorphone hydrochloride, levorphanol, alfentanil hydrochloride, meperidine, meperidine hydrochloride, methadone, morphine, nalbuphine, opium, levomethadyl, hyaluronate sodium, sufentanil citrate, capsaicin, tramadol, leflunomide, oxycodone, oxymorphone, celecoxib, pentazocine, propoxyphene, benzocaine, lidocaine, dezocine, clonidine, butalbital, phenobarbital, tetracaine, phenazopyridine, sulfamethoxazole/phenazopyridine, and sulfisoxazole/phenazopyridine.

In some embodiments, the present invention provides the delivery of anticoagulants, including, but not limited to, coumarins, 1,3-indandione, anisindione, fondaparinux, heparin, lepirudin, antithrombin, warfarin, enoxaparin, dipyridamole, dalteparin, ardeparin, nadroparin, and tinzaparin.

In some embodiments, the present invention provides the delivery of coagulation factors, including, but not limited to, Factor I (fibrinogen), Factor II (prothrombin), Factor III (thromboplastin, tissue factor), Factor IV (calcium), Factor V (labile factor), Factor VII (stable factor), Factor VIII (antihemophilic globulin, antihemophilic globulin, antihemophilic factor A), Factor IX (plasma thromboplastin component, Christmas factor, antihemophilic factor B), Factor X (Stuart factor, Prower factor, Stuart-Prower factor), Factor XI (plasma thromboplastin antecedent, antihemophilic factor C), Factor XII (Hageman factor, surface factor, contact factor), and Factor XIII (fibrin stabilizing factor, fibrin stabilizing enzyme, fibri-nase).

In some embodiments, the present invention provides the delivery of anti-inflammatory agents, including, but not limited to, non-steroidal anti-inflammatory drugs (NSAIDs) including diclofenac (also known as Voltaren, Abitren, Allvoran, Almiral, Alonpin, Anfenax, Artrites, Betaren, Blesin, Bolabomin, Cataflam, Clofec, Clofen, Cordralan, Curinflam, Diclomax, Diclosian, Dicsnal, Difenac, Ecofenac, Hizemin, Inflamac, Inflanac, Klotaren, Lidonin, Monoflam, Naboal, Oritaren, Remethan, Savismin, Silino, Staren, Tsudohmin, Voltarol, Voren, Voveran, and Vurdon), diflunisal (also known as Dolobid, Adomal, Diflonid, Diflunil, Dolisal, Dolobis, Dolocid, Donobid, Dopanone, Dorbid, Dugodol, Flovacil, Fluniget, Fluodonil, Flustar, Ilacen, Noaldol, Reuflos, and Unisal), etodolac (also known as Lodine), fenoprofen (also known as Nalfon, Fenoprex, Fenopron, Fepron, Nalgesic, and Progesic), flurbiprofen (also known as Ansaid and Ocuflur), ibuprofen (also known as Rufen, Motrin, Aches-N-Pain, Advil, Nuprin, Dolgesic, Genpril, Haltran, Ibifon, Ibren, Ibumed, Ibuprin, Ibupro-600, Ibuprohm, IbuTab, Ibutex, Ifen, Medipren, Midol 200, Motrin-IB, Cramp End, Profen, Ro-Profen, Trendar, Alaxan, Brofen, Alfam, Brufen, Algofen, Brufort, Amersol, Bruzon, Andran, Buburone, Anflagen, Butacortelone, Apsifen, Deflem, Artofen, Dolgit, Artril, Dolocyl, Bloom, Donjust, Bluton, Easifon, Ebufac, Emflam, Emodin, Fenbid, Fenspan, Focus, Ibosure, Ibufen, Ibufug, Ibugen, Ibumetin, Ibupirac, Imbun, Inabrin, Inflam, Irfen, Librofen, Limidon, Lopane, Mynosedin, Napacetin, Nobafon, Nobgen, Novogent, Novoprofen, Nurofen, Optifen, Paduden, Paxofen, Perofen, Proartinal, Prontalgin, Q-Profen, Relcofen, Remofen, Roidenin, Seclodin, Tarein, and Zofen), indomethacin (also known as Indameth, Indocin, Amuno, Antalgin, Areumatin, Argilex, Artherexin, Arthrexin, Artrinovo, Bavilon, Bonidon, Boutycin, Chrono-Indocid, Cidalgon, Confortid, Confortind, Domecid, Durametacin, Elemetacin, Idicin, Imbrilon, Inacid, Indacin, Indecin, Indocap, Indocen, Indocid, Indoflex, Indolag, Indolar, Indomed, Indomee, Indometacinum, Indometicina, Indometin, Indovis, Indox, Indozu, Indrenin, Indylon, Inflazon, Inpan, Lauzit, Liometace, Metacen, Metindon, Metocid, Mezolin, Mobilan, Novomethacin, Peralgon, Reflox, Rheumacid, Rheumacin, Salinac, Servindomet, Toshisan, and Vonum), ketoprofen (also known as Orudis, Alrheumat, Alrheumun, Alrhumat, Aneol, Arcental, Dexal, Epatec, Fastum, Keduril, Kefenid, Keprofen, Ketofen, Ketonal, Ketosolan, Kevadon, Mero, Naxal, Oruvail, Profenid, Salient, Tofen, and Treosin), ketorolac (also known as Toradol), meclofenamate (also known as Meclofen, Meclomen, and Movens), mefenamic acid (also known as Ponstel, Alpain, Aprostal, Benostan, Bonabol, Coslan, Dysman, Dyspen, Ecopan, Lysalgo, Manic, Mefac, Mefic, Mefix, Parkemed, Pondex, Ponsfen, Ponstan, Ponstyl, Pontal, Ralgec, and Youfenam), nabumetone (also known as Relafen), naproxen (also known as Naprosyn, Anaprox, Aleve, Apranax, Apronax, Arthrisil, Artrixen, Artroxen, Bonyl, Congex, Danaprox, Diocodal, Dysmenalgit, Femex, Flanax, Flexipen, Floginax, Gibixen, Headlon, Laraflex, Laser, Leniartil, Nafasol, Naixan, Nalyxan, Napoton, Napren, Naprelan, Naprium, Naprius, Naprontag, Naprux, Napxen, Narma, Naxen, Naxid, Novonaprox, Nycopren, Patxen, Prexan, Prodexin, Rahsen, Roxen, Saritilron, Sinartrin, Sinton, Sutony, Synflex, Tohexen, Veradol, Vinsen, and Xenar), oxaprozin (also known as Daypro), piroxicam (also known as Feldene, Algidol, Antiflog, Arpyrox, Atidem, Bestocam, Butacinon, Desinflam, Dixonal, Doblexan, Dolonex, Feline, Felrox, Fuldin, Indene, Infeld, Inflamene, Lampoflex, Larapam, Medoptil, Novopirocam, Osteral, Pilox, Piraldene, Piram, Pirax, Piricam, Pirocam, Pirocaps, Piroxan, Piroxedol, Piroxim, Piton, Posidene, Pyroxy, Reucam, Rexicam, Riacen, Rosic, Sinalgico, Sotilen, Stopen, and Zunden), sulindac (also known as Clinoril, Aflodac, Algocetil, Antribid, Arthridex, Arthrocine, Biflace, Citireuma, Clisundac, Imbaral, Lindak, Lyndak, Mobilin, Reumofil, Sudac, Sulene, Sulic, Sulindal, Suloril, and Sulreuma), tolmetin (also known as Tolectin, Donison, Midocil, Reutol, and Safitex), celecoxib (also known as Celebrex), meloxicam (also known as Mobic), rofecoxib (also known as Vioxx), valdecoxib (also known as Bextra), aspirin (also known as Anacin, Ascriptin, Bayer, Bufferin, Ecotrin, and Excedrin) and steroidal anti-inflammatory drugs including cortisone, prednisone and dexamethasone.

In some embodiments, the present invention provides the delivery of vasoconstrictors, including, but not limited to, epinephrine (adrenaline, Susphrine), phenylephrine hydrochloride (Neo-Synephrine), oxymetazoline hydrochloride (Afrin), norepinephrine (Levophed), and caffeine.

In some embodiments, the present invention provides the delivery of vasodilators, including, but not limited to, bosentan (Tracleer), epoprostenol (Flolan), treprostinil (Remodulin), sitaxsentan, nifedipine (Adalat, Procardia), nicardipine (Cardene), verapamil (Calan, Covera-HS, Isoptin, Verelan), diltiazem (Dilacor XR, Diltia XT, Tiamate, Tiazac, Cardizem), isradipine (DynaCirc), nimodipine (Nimotop), amlodipine (Norvasc), felodipine (Plendil), nisoldipine (Sular), bepridil (Vascor), hydralazine (Apresoline), minoxidil (Loniten), isosorbide dinitrate (Dilatrate-SR, Iso-Bid, Isonate, Isorbid, Isordil, Isotrate, Sorbitrate), isorbide mononitrate (IMDUR), prazosin (Minipress), cilostazol (Pletal), treprostinil (Remodulin), cyclandelate, isoxsuprine (Vasodilan), nylidrin (Arlidin), nitrates (Deponit, Minitran, Nitro-Bid, Nitrodisc, Nitro-Dur, Nitrol, Transderm-Nitro), benazepril (Lotensin), benazepril and hydrochlorothiazide (Lotensin HCT), captopril (Capoten), captopril and hydrochlorothiazide (Capozide), enalapril (Vasotec), enalapril and hydrochlorothiazide (Vaseretic), fosinopril (Monopril), lisinopril (Prinivil, Zestril), lisinopril and hydrochlorothiazide (Prinzide, Zestoretic), moexipril (Univasc), moexipril and hydrochlorothiazide (Uniretic), perindopril (Aceon), quinapril (Accupril), quinapril and hydrochlorothiazide (Accuretic), ramipril (Altace), trandolapril (Mavik), papaverine (Cerespan, Genabid, Pavabid, Pavabid HP, Pavacels, Pavacot, Pavagen, Pavarine, Pavased, Pavatine, Pavatym, Paverolan).

In some embodiments, the present invention provides the delivery of diuretics, including, but not limited to, acetazolamide (Diamox), dichlorphenamide (Daranide), methazolamide (Neptazane), bendroflumethiazide (Naturetin), benzthiazide (Exna), chlorothiazide (Diuril), chlorthalidone (Hygroton), hydrochlorothiazide (Esidrix, HydroDiuril, Microzide), hydroflumethiazide (Diucardin), indapamide (Lozol), methyclothiazide (Enduron), metolazone (Zaroxolyn, Mykrox), polythiazide (Renese), quinethazone (Hydromox), trichlormethiazide (Naqua), bumetanide (Bumex), ethacrynic acid (Edecrin), furosemide (Lasix), torsemide (Demadex), amiloride (Midamor), amiloride and hydrochlorothiazide (Moduretic), spironolactone (Aldactone), spironolactone and hydrochlorothiazide (Aldactazide), triamterene (Dyrenium), triamterene and hydrochlorothiazide (Dyazide, Maxzide).

In some embodiments, the present invention provides the delivery of anti-cancer agents, including, but not limited to, aldesleukin, alemtuzumab, alitretinoin, allopurinol, altretamine, amifostine, anagrelide, anastrozole, arsenic trioxide, asparaginase, bexarotene, bicalutamide, bleomycin, busulfan, calusterone, capecitabine, carboplatin, carmustine, celecoxib, chlorambucil, cisplatin, cladribine, cyclophosphamide, cytarabine, dacarbazine, dactinomycin, darbepoetin alpha, daunorubicin, daunomycin, dexrazoxane, docetaxel, doxorubicin, epoetin alpha, estramustine, etoposide, etoposide phosphate, exemestane, filgrastim, floxuridine, fludarabine, flutamide, fulvestrant, gemcitabine, gemtuzumab ozogamicin, goserelin acetate, hydroxyurea, ibritumomab tiuxetan, idarubicin, ifosfamide, imatinib mesylate, interferon alpha-2a, interferon alpha-2b, irinotecan, leflunomide, letrozole, leucovorin, levamisole, lomustine, meclorethamine (nitrogen mustard), megestrol acetate, melphalan, mercaptopurine, mesna, methotrexate, methoxsalen, mitomycin C, mitotane, mitoxantrone, mycophenolate mofetil, nandrolone phenpropionate, nilutamide, nofetumomab, oprelvekin, oxaliplatin, paclitaxel, pamidronate, pegademase, pegaspargase, pegfilgrastim, pentostatin, pipobroman, plicamycin, porfimer sodium, procarbazine, quinacrine, rasburicase rituximab, sargramostim, streptozocin, tacrolimus, tamoxifen, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In some embodiments, the compositions and systems of the present invention incorporate analgesics. Analgesics include but are not limited to topical anesthetic agents such as lidocaine, bupivicaine, proparicane, tetracaine, prilocaine, oxybuprocaine and the like. A large number of commercial formulations, alone and in combination with other anesthetic and other agents are commercially available (see: www.drugs.com/drug-class/topical-anesthetics.html). Topical analgesic include but are not limited to morphine and its derivatives, cocaine and its derivative, capsaicin (the active ingredients of hot peppers), specific inhibitors of capsaicin responding receptors (such as TrpV1). Transient Receptor Potential (TRP) channel Vanilloid 1 (TRPV1) as a target for treating chronic pain. TRPV1 is a multifunctional channel involved in thermosensation (heat) and taste perception (e.g. peppers and vinegar). Importantly, TRPV1 also functions as a molecular integrator for a broad variety of seemingly unrelated noxious stimuli. Desensitization to topical TRPV1 agonists (e.g. capsaicin creams and patches) has been in clinical use for decades to treat chronic painful conditions like diabetic neuropathy. Resiniferatoxin has shown efficacy. Currently, site-specific capsaicin and resiniferatoxin (an ultrapotent capsaicin analog) injections are being evaluated as "molecular scalpels" to achieve permanent analgesia. Most recently, a number of potent, small molecule TRPV1 antagonists have been advanced into clinical trials for pain relief.

Analgesic therapies for acute and chronic pain conditions currently rely on three major classes of drugs: nonsteroidal anti-inflammatory drugs (NSAIDs), opioids, and a group of drugs with diverse pharmacological actions many of which are frequently referred to as adjuvants (e.g., antidepressants, anticonvulsants, local anesthetics, $\alpha_2$-adrenoceptor agonists, capsaicin and its derivatives). A variety of analgesics have been used topically and are useful as active agents that can be integrated into the compositions, formulations and systems of the present invention. It is contemplated that an inflammatory state of cellular elements of the mucous membrane as well as a pro-inflammatory thin film (containing pro-inflammatory mediators) will have an altered chemistry and/or biophysical attributes that would alter its interfacial properties as to degrade the quality and/or stability of the thin film cellular interface. Therefore the integration of anti-inflammatory agents such as steroids, cyclosporins and non-steroisdal anti-inflammatory agents (e.g., Cox 1, cox 2 inhibitors) would improve surface attributes of the cellular components of mucous membranes and improve thin film stability.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A composition for modifying a mucous membrane comprising a first agent that physically interacts or reacts with a protein in said mucous membrane and/or its intimately associated adherent thin film, a second agent that promotes holding an aqueous component of said mucous membrane in place, and a physiologically acceptable carrier wherein said first agent is a peptide, polypeptide or protein modified to comprise a heterobifunctional linker and said second agent is a mucin or mucin analog.

2. The composition of claim 1, wherein said physiologically acceptable carrier is compatible with a mucous membrane.

3. The composition of claim 1, wherein said intimately adherent thin film is selected from the group consisting of a tear film, vaginal secretion and salivary constituent.

4. The composition of claim 1, wherein the heterobifunctional linker is selected from the group consisting of N-succinimidyl 3-(2-pyridyldithio)propionate, succinimidyl 6-(3-[2-pyridyldithiol-propionamido)hexanoate, sulfosuccinimidyl 6-(3'-[2-pyridyldithiol-propionamido)hexanoate, succinimidyloxycarbonyl-α-methyl-α-(2-pyridyldithio)toluene, sulfosuccinimidyl-6[α-methyl-α-(2-pyridyldithio)toluamidolhexanoate, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxy-sulfosuccinimide ester, N-succinimidyl(4-iodoacetyl)aminobenzoate, sulfo-succinimidyl(4-iodoacetyl)aminobenzoate, succinimidyl-4-(p-maleimidophenyl)butyrate, sulfosuccinimidyl-4-(p-maleimidophenyl)butyrate, N-(γ-maleimidobutyryloxy)succinimide ester, N-(γ-maleimidobutyryloxy)sulfosuccinimide ester, succinimidyl 6-((iodoacetyl)amino)hexanoate, succinimidyl 6-(6-((((4-iodoacetyl)amino)hexanoyl)amino)hexanoate, succinimidyl 4-(((iodoacetyl)amino)methyl)cyclohexane-1-carboxylate, succinimidyl 6-((((4-iodoacetyl)amino)methyl)cyclohexane-1-carbonyl)amino)-hexanoate, and p-nitrophenyl iodoacetate.

5. A topical formulation comprising the composition of claim 1.

\* \* \* \* \*

UNITED STATES PATENT AND TRADEMARK OFFICE
CERTIFICATE OF CORRECTION

PATENT NO.         : 11,712,423 B2
APPLICATION NO.    : 17/222089
DATED              : August 1, 2023
INVENTOR(S)        : Nicholas L. Abbott and Christopher J. Murphy It is certified that error appears in the above-identified patent and that said Letters Patent is hereby corrected as shown below:

In the Claims

Column 41, Claim 4, Line 52 reads:
[2-pyridyldithiol-propionamido)hexanoate, sulfosuccinimi-
Whereas it should read:
[2-pyridyldithio]-propionamido)hexanoate, sulfosuccinimi- Column 41, Claim 4, Line 53 reads:
dyl 6-(3'-[2-pyridyldithiol-propionamido)hexanoate, succin
Whereas it should read:
dyl 6-(3'-[2-pyridyldithio]-propionamido)hexanoate, succin Column 42, Claim 4, Line 35 reads:
dolhexanoate, succinimidyl 4-(N-maleimidomethyl)cyclo
Whereas it should read:
do]hexanoate, succinimidyl 4-(N-maleimidomethyl)cyclo Signed and Sealed this
Seventh Day of May, 2024

Katherine Kelly Vidal
*Director of the United States Patent and Trademark Office*